United States Patent [19]
Love

[11] Patent Number: 6,129,758
[45] Date of Patent: Oct. 10, 2000

[54] PRODUCTS AND METHODS FOR CIRCULATORY SYSTEM VALVE REPAIR

[75] Inventor: Jack W. Love, Santa Barbara, Calif.

[73] Assignee: CardioMend LLC, Santa Barbara, Calif.

[21] Appl. No.: 08/726,342

[22] Filed: Oct. 3, 1996

Related U.S. Application Data

[63] Continuation-in-part of application No. 08/539,971, Oct. 6, 1995, Pat. No. 5,716,399.

[51] Int. Cl.[7] .................................................. A61F 2/24
[52] U.S. Cl. ............................................... 623/2.11
[58] Field of Search ........................................ 623/2, 2.11

[56] References Cited

U.S. PATENT DOCUMENTS

| | | |
|---|---|---|
| 3,320,972 | 5/1967 | High et al. . |
| 3,655,306 | 4/1972 | Ross et al. . |
| 4,470,157 | 9/1984 | Love . |
| 4,731,075 | 3/1988 | Gallo Mezo et al. . |
| 4,960,424 | 10/1992 | Grooters . |
| 5,147,391 | 9/1992 | Lane . |
| 5,156,621 | 10/1992 | Navia et al. . |
| 5,163,955 | 11/1992 | Love et al. . |
| 5,197,979 | 3/1993 | Quintero et al. . |
| 5,258,021 | 11/1993 | Duran . |
| 5,326,370 | 7/1994 | Love et al. . |
| 5,326,371 | 7/1994 | Love et al. . |
| 5,336,258 | 8/1994 | Quintero et al. . |
| 5,344,442 | 9/1994 | Deac . |
| 5,352,240 | 10/1994 | Ross . |
| 5,370,685 | 12/1994 | Stevens . |
| 5,376,112 | 12/1994 | Duran . |
| 5,411,552 | 5/1995 | Anderson et al. . |
| 5,425,741 | 6/1995 | Lemp et al. . |
| 5,449,384 | 9/1995 | Johnson . |
| 5,480,424 | 1/1996 | Cox . |
| 5,503,638 | 4/1996 | Cooper et al. . |

FOREIGN PATENT DOCUMENTS

| | | |
|---|---|---|
| 8507491 | 8/1991 | Australia . |
| 0581233 | 2/1994 | European Pat. Off. . |
| 2399832 | 3/1979 | France . |
| 9203990 | 3/1992 | WIPO . |
| 9212690 | 6/1992 | WIPO . |
| 9213502 | 8/1992 | WIPO . |
| 9318721 | 9/1993 | WIPO . |
| 9516411 | 6/1995 | WIPO . |

OTHER PUBLICATIONS

Acar et al., "Surgery for Acquired Heart Disease," *Journal of Thoracic and Cardiovascular Surgery* 111:367–380 (1996).

Aupart et al., "New Procedure to Replace the Aortic Valve With Autologous Pericardium: A Clinical Case," *Ann Thorac Surg* 58:245–247 (1994).

Borowski et al., "Mitral Valve Remodeling Using Autologous Pericardium: An Experimental Study," *Ann Thorac Surg* 58:452–457 (1994).

Chauvaud et al., "Valve extension with glutaraldehyde–preserved autologous pericardium," *Journal of Thoracic and Cardiovascular Surgery* 102:171–178 (1991).

Duran et al., "Haemodynamic Effect of Supraaortic Ridge Enchancement on the Closure Mechanism of the Aortic Valve and Its Implications in Aortic Valve Repair," *Thorac. Cardiovasc. Surgeon* 38:6–9 (1990).

Duran et al., "Indications and Limitations of Aortic Valve Reconstruction," *Ann Thorac Surg* 52:447–454 (1991).

Duran et al., "Long–term results of conservative repair of rheumatic aortic valve insufficiency," *Eur. J. Cardio–thorac Surg.* 2:217–223 (1988).

Duran, "Reconstructive Techniques for Rheumatic Aortic Valve Disease," *Journal of Cardiac Surgery* 3:23–28 (1988).

(List continued on next page.)

*Primary Examiner*—Michael J. Milano
*Attorney, Agent, or Firm*—Bryan Cavee LLP

[57] ABSTRACT

A standardized and reproducible method and instruments related thereto for repair of atrio-ventricular, aortic and pulmonary valves is provided.

11 Claims, 17 Drawing Sheets

OTHER PUBLICATIONS

Gott et al., "Calcification of Porcine Valves: A Successful New Method of Antimineralization," *Ann Thorac Surg* 53:207–216 (1992).

Lillehei et al., "Mitral Valve Replacement With Preservation of Papillary Muscles and Chordae Tendineae," *Journal of Thoracic and Cardiovascular Surgery* 47:532–543 (1964).

Love, *Autologous Tissue Heart Valves*, R.G. Landes Company, Austin, pp. 1–120 (1993).

Love et al., "Ch 10—An Autologous Tissue Bioprosthetic Heart Valve," in *New Horizons and the Future of Heart Valve Bioprostheses*, edited by Gabbay and Fratgr, Silent Partners, Inc., Austin, Texas, pp. 135–141 (1994).

Love et al., "Ch. 74—Rapid Intraoperative Fabrication of an Autogenous Tissue Heart Valve: A New Technique," Biologic & Bioprosthetic Valves: Proceedings of the Third International Symposium, New York, Yorke Medical Books, pp. 691–698 (1986).

Love, "An Alternative Method for Applying a Dacron Cover to a Delrin Bioprosthetic Heart Valve Stent," Biomedical Engineering III—Recent Developments: Proceedings of the Third Southern Biomedical Engineering Conference pp. 30–37 (1984).

Love et al., "Experimental Evaluation of an Autologous Tissue Heart Valve," *Journal of the Heart Valve Disease* 1:232–241 (1992).

Love et al., "Autogenous Tissue Valve Replacement in the Canine," *ASAIO Abstracts*, p. 32 (1992).

Love et al., "The Autogenous Tissue Heart Valve: Current Status," *Journal of Cardiac Surgery* 6:499–507 (1991).

Love et al., "Degenerative calcification in tissue valves—a metabolic/hemodynamic or immunologic problem?" Abstract published for *First Scientific Meeting of the International Association for Cardiac Biological Implants*, Palmer House Hotel, Chicago, Illinois, Sunday, Apr. 5 (1987).

Love et al., "Improved Bioprosthetic Heart Valve Durability," *Asaio Abstracts*, p. 32 (1992).

Love et al., "The Autogenous Tissue Heart Valve: Experience with Pericardium," Proceedings of the Interational Symposium of the Austrian Society for Thoracic and Cardiovascular Surgery as a Heart Valve Substitute. Is it Living Up to It's Promise?, Symbion, Inc., Salt Lake City, UT, pp. 31–40 (1989).

Sands et al., "An Anatomical Comparison of Human, Pig, Calf and Sheep Aortic Valves," *Ann Thorac Surg* 8:407–414 (1969).

Senning, "Fascia lata replacement of aortic valves," *Journal of Thoracic and Cardiovascular Surgery* 54:465–470 (1967).

Senning, "Ch. 13—Alterations in Valvular Surgery: Biologic Valves," Cardiac Bioprostheses: Proceedings of the Second International Symposium, Yorke Medical Books, pp. 144–153.

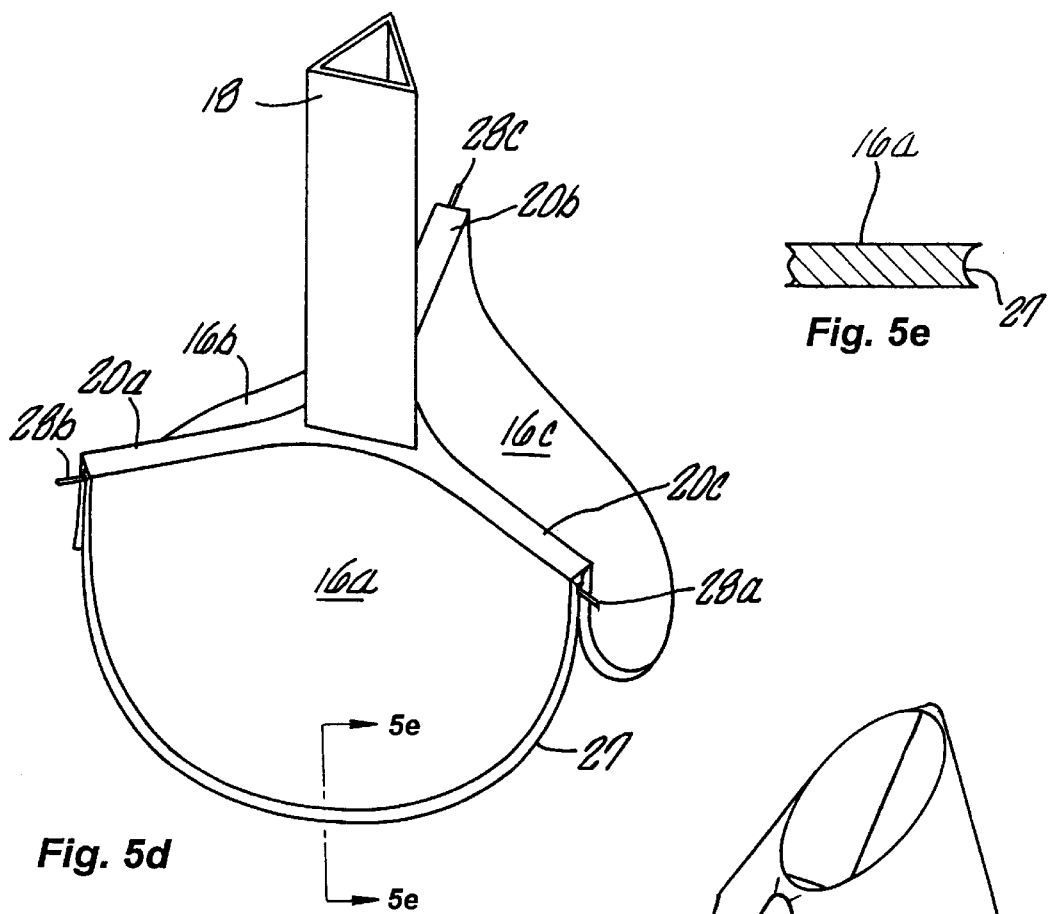
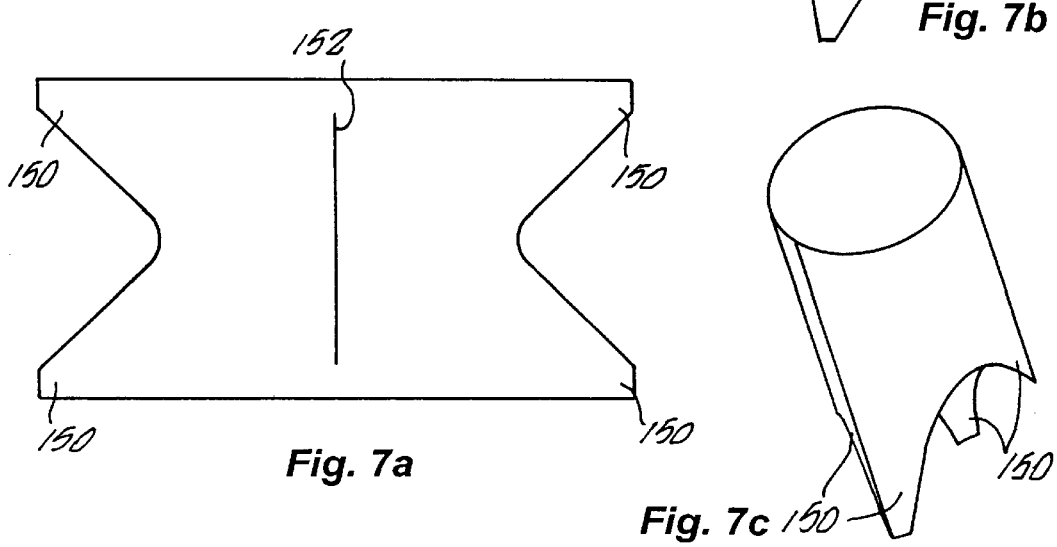

PRODUCTS AND METHODS FOR CIRCULATORY SYSTEM VALVE REPAIR

CROSS REFERENCE TO RELATED APPLICATIONS

This application is a Continuation-In-Part of pending U.S. application Ser. No. 08/539,971 filed Oct. 6, 1995 in the name of Jack W. Love, which is fully incorporated by reference herein now U.S. Pat. No. 5,716,399.

FIELD OF THE INVENTION

This invention relates generally to methods of heart valve repair. More specifically, this invention relates to methods of heart valve repair which are standardized and thus more easily replicated in the limited time available while the patient is on the operating table.

BACKGROUND OF THE INVENTION

For over thirty-five years it has been possible to replace heart valves, since the advent of the heart-lung machine and various mechanical and tissue heart replacement heart valves designed by surgeons and engineers.

The concept of repairing, rather than replacing, diseased heart valves began with the work of Professor Åke Senning of Zurich in 1960. (Senning Å:Fascia lata replacement of aortic valves. *J Thorac Cardiovasc Surg* 54:465–470 (1967)). Senning used autologous fascia lata to fashion both aortic valve repairs and replacements with a freehand technique, but subsequently abandoned his method by 1970 because of valve failures from thickening and shrinkage of the fresh, untreated tissue.

The concept of valve repair with autologous tissue was resurrected by Professor Alain Carpentier of Paris. Beginning in 1980, he began work with the repair of mitral valve leaflets damaged by rheumatic heart disease, using gusset patches of autologous pericardium treated with a brief immersion in glutaraldehyde. In 1991, Carpentier reported a series of 64 patients who had mitral leaflet augmentation by this technique from 1980 to 1989, with excellent results. (Chauvaud S, Jebara V, Chachques J-C, Asmar BE, Mihaileanu S, Perier P, Dreyfus G, Relland J, Couetil J-P, Carpentier A "Valve extension with glutaraldehyde-preserved autologous pericardium." *J Thorac Cardiovasc Surg* 102:171–178 (1991)). Importantly, he was able to report that the autologous tissue treated with glutaraldehyde did not thicken or shrink or calcify, up to ten years after implantation for repair. In addition to this method for leaflet augmentation, Carpentier employs a combination of annuloplasty, leaflet resection, and chordal shortening and re-implantation techniques to repair mitral valves.

Duran has used autologous pericardium treated with a brief immersion in glutaraldehyde for repair of diseased aortic valves, with good results, including lack of calcification. (Duran C, Kumar N, Gometza B, Al Halees Z; "Indications and limitations of aortic valve reconstruction." *Ann Thorac Surg* 52:447–454 (1991)).

A problem with all these approaches, however, is that they were not standardized and thus could not easily be replicated in the limited time available while the patient was on the operating table. As described in U.S. Pat. Nos. 5,326,371; 5,163,955; 5,326,370; and 4,470,157, all of which are incorporated by reference herein as though set forth in full, standardized approaches to valve replacement (in contrast to valve repair) are available. However, such approaches involve the use of a stent.

The problem with a stent-mounted prosthesis is that the stent occupies space, and thereby reduces the effective orifice area of the valve. Another disadvantage is that a stent is foreign material. Prosthetic valve infection is not common, but when it occurs, it is a catastrophic complication. A prosthesis of non-biological material must be replaced, in almost all cases, if it becomes infected.

Bailey pioneered concepts for repair and reconstruction of mitral valves with atrial wall tissue and fascia lata. Carpentier expanded on his concepts with methods for chordal and leaflet repair and annular support of the mitral valve. He first used fully tanned bovine pericardium for this leaflet repairs, but later switched to lightly tanned autologous pericardium because of increasing evidence that the material was durable and resistant to calcific degeneration. More recently, Borowski and his colleagues have reported experimental work with reconstruction concepts that they refer to as remodeling of the mitral valve with lightly tanned autologous pericardium, what they refer to as "a perfect prosthetic material" on the basis of experimental work reported by Love. (Borowski, et al. *Ann. Thorac. Surg.* 58: 452–57 (1994)) There is a lack of standardization in such repairs, since their technique is essentially free-hand method for leaflet reconstruction without any chordal repair.

Accordingly, it is an object of the invention to provide a method of and apparatus for valve repair which overcomes the disadvantages of the prior art.

The anatomy of the atrioventricular valves (mitral and tricuspid) is different from that of the semilunar cardiac outflow valves (aortic and pulmonic). Whereas the former have irregular geometry with leaflet support provided by annular attachment and chordae tendineae connecting the leaflet free edges to the papillary muscles within the ventricles, the latter have an essentially symmetrical trileaflet geometry with leaflet support provided by the scalloped annular attachment and the fixed length of the leaflet free edges extending from the commissures. With regard to the atrioventricular valves, there is increasing recognition that the chordal apparatus should be maintained for optimal ventricular function, a suggestion first made by Lillehei. (Lillehei, *J. Thorac. and Cardiovascular Surg.* 47:532–43 (1964)) That means that an ideal prosthetic atrioventricular valve, or any method for repairing or reconstructing an atrioventricular valve, should incorporate or retain the connection of the valve to the papillary muscles of the ventricular wall through the leaflets and chordae tendineae (i.e. retain annulo-papillary continuity). Mechanical valves cannot satisfy this requirement, and bioprosthetic valves are generally stent-mounted, without chordal apparatus. There have been several reports of bioprosthesis designs with chordal mechanisms (tested in the animal laboratory and/or clinically), by, e.g., McPhail; Hofelder; Edwards; Mickleborough; Frater; and, Cox (U.S. Pat. No. 5,480,424). Deac modified the concepts of Hofelder and Edwards, and Mickleborough, to make a stentless mitral valve prosthesis with chordal apparatus (U.S. Pat. No. 5,344,442). The problems with all of the reported methods for mitral valve replacement or reconstruction have been lack of precision and reproducibility, lack of standardized instrumentation to facilitate the valve reconstructions, and lack of suitable material for the reconstructions. There has more recently been a report of mitral replacements, but not repair, with homograft tissue. (Acar, et al., *J. Thorac. Cardiovascular Surgery* 111(2):367–80 (February, 1996))

Love and colleagues suggested in 1985 that autologous pericardium treated with a brief immersion in dilute glutaraldehyde solution would be a suitable valve repair material. Work by his group, and that of others including Carpentier, Duran and Deac, has shown that autologous pericardium so treated is resistant to calcific degeneration in the juvenile sheep model, and in humans who have undergone valve repair, reconstruction or replacement with that material. Good long term results are being obtained with current generation bovine pericardial bioprostheses in older patients, suggesting that homologous or heterologous repair tissue could be used with that older patient cohort.

There is a need for methodology and surgical instruments for cutting a precisely sized and shaped geometric pattern with which an atrioventricular valve reconstruction can be accomplished, and which will facilitate the reconstruction in a manner that will expedite and standardize the reconstruction. Ideally, the surgical instruments used for the reconstruction are simple, inexpensive, disposable or reusable and available in a full range of sizes.

BRIEF DESCRIPTION OF THE DRAWINGS

FIGS. 5a–5e illustrate the use of a continuous pledget reinforcing strip in the context of the subject invention.

FIGS. 7a–c depict a pattern for use in preparing atrioventricular repair material. The pattern provides a configuration to fashion a cylindrical shape from a flat piece of tissue without an annular seam. FIG. 7a depicts a flat tissue pattern; FIG. 7b depicts the pattern of FIG. 7a partially folded; FIG. 7c depicts the finished cylindrical shape of the folded repair material.

In all the aforementioned figures, like elements are referenced with like identifying numerals.

SUMMARY OF THE INVENTION

Figure 1:
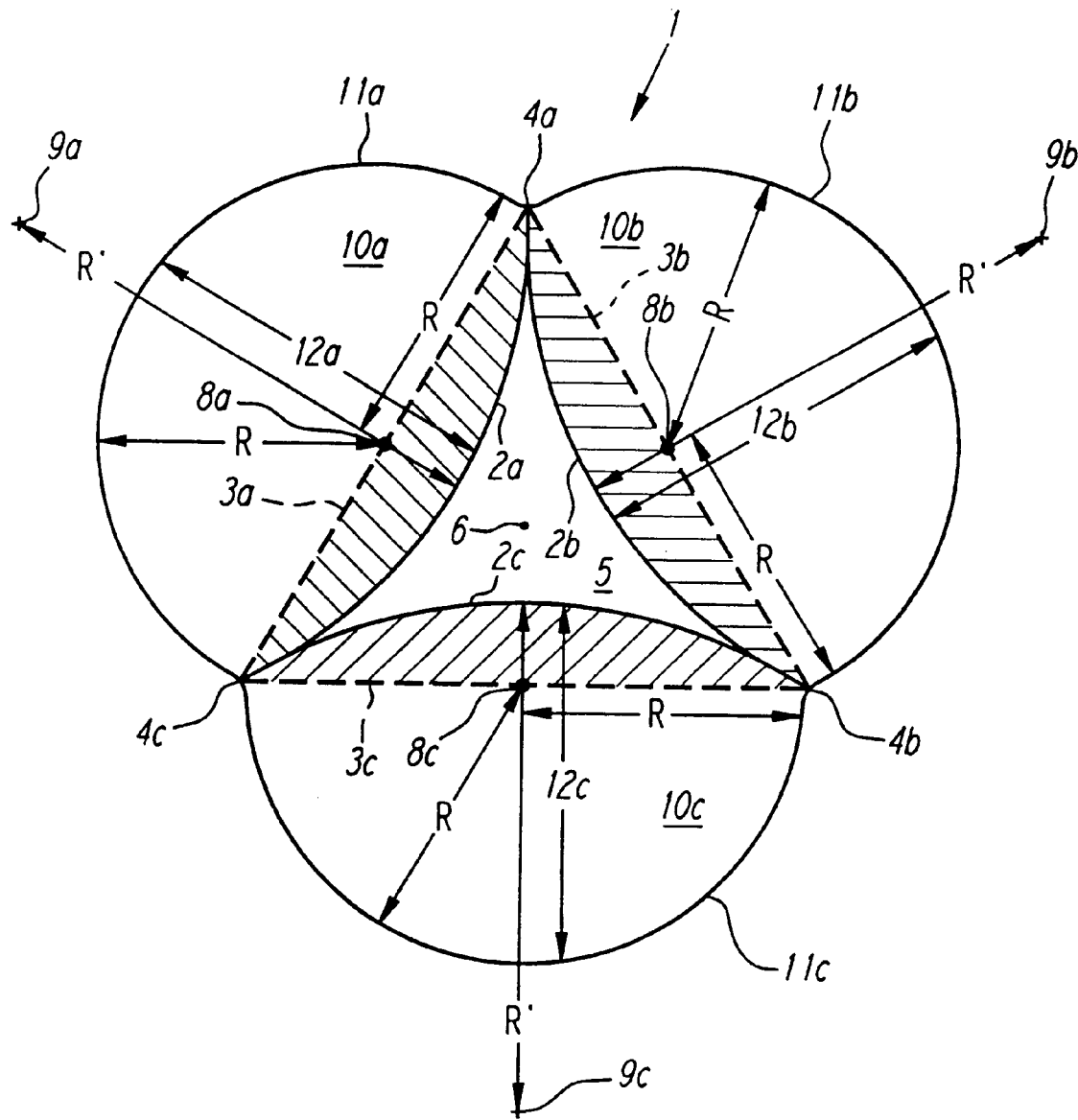
FIG. 1 illustrates the preferred trefoil tissue pattern for use with the subject invention.

A valve reconstruction or repair, by definition, will not require a stent. This application addresses the need for methods to measure and cut proper patterns of autologous, homologous or-heterologous tissue, and surgical instruments that can be used to hold and or form the tissue temporarily during the repair or reconstruction operative procedure. The disposable or reusable instruments, or formers, hold the tissue in an anatomically correct orientation, whereby the surgeon can perform a more precise repair or reconstruction.

To achieve the objects, and in accordance with the purpose of the invention as described in detail herein, there is disclosed a former comprising a first tissue forming surface, wherein the first tissue forming surface is complementary and engagable to a second tissue forming surface, whereby when tissue is placed between the first tissue forming surface and the second tissue forming surface and the tissue forming surfaces are brought into complementary engagement, the tissue is held in a form capable of being used as a valve repair material for a circulatory system valve.

Also disclosed herein is a surgical instrument comprising a means for holding a piece of tissue in a configuration of at least one leaflet of a closed or partially closed circulatory system valve.

Also disclosed herein is a tissue cutting pattern comprising a configuration that delimits a two dimensional area that corresponds to the shape of tissue to be used in a repair of at least one leaflet of a circulatory system valve, wherein the die delimits more than one segment, and up to all three segments, of a three segment trefoil shape. The trefoil tissue cutting pattern can comprise a configuration that delimits three lobes arranged in substantial radial symmetry about a central coaption point within a central aperture, the central aperture delimited by coaptive edges, whereby when tissue is cut along edges of the pattern, coaptive edges of the cut tissue can meet at a central coaption point when the tissue is held as a valve in a closed position. The trefoil tissue cutting pattern can comprise a configuration that delimits three lobes and each lobe meets adjacent lobes at commissure areas, and the lobes are configured to provide extra coaptive surfaces of tissue cut by use of the die, whereby when tissue is cut along edges of the pattern a central coaption point of the cut tissue lies above a plane defined by the commissure areas.

The tissue cutting pattern of the invention can be defined by a cutting edge of a tissue cutting die, or be defined by a margin of a template.

Also disclosed herein is a tissue cutting pattern comprising a configuration that delimits a two dimensional area that corresponds to a shape of tissue to be used in a repair of at least one leaflet of an atrioventricular valve, said pattern further comprising a two dimensional area that corresponds to a shape of tissue to be used in a repair of a chordal apparatus.

Also disclosed herein is a kit comprising: a first tissue forming surface; and, a second tissue forming surface, wherein the second tissue forming surface is complementary to the first tissue forming surface. The kit can comprise a tissue cutting die or tissue cutting template, a tool for harvesting tissue from the patient, a basin for treatment of harvested tissue, or a tool for sizing an annulus of a circulatory system valve to be repaired. The prefabricated kit can be made to contain components that are size specific to a particular valve to be repaired.

Also disclosed herein is a method for repairing a circulatory system valve comprising: a) sizing an annulus in a circulatory system; (b) providing tissue; (c) cutting the tissue; (d) forming said cut tissue into a shape suitable for repair of a circulatory system valve; and, (e) suturing the formed tissue to the annulus. The method can comprise a step of treating the tissue.

Also disclosed herein is a method to produce material for repairing a circulatory system valve, said method comprising steps of: sizing an annulus in a circulatory system at a repair site; providing tissue; cutting at least a portion of a trefoil pattern from the tissue, wherein the pattern is matched to the size of the annulus; providing complementary first and second tissue forming surfaces, wherein the surfaces are matched to the size of the annulus of the valve; forming a valve repair material from said trefoil pattern by engaging the first forming surface to said second tissue forming surface with said cut tissue pattern sandwiched therebetween.

Also disclosed herein is a method to produce a material for repairing a mitral valve, said method comprising steps of: sizing an annulus at a mitral valve repair site; providing autologous, homologous or heterologous tissue; cutting a pattern from the tissue, whereby the cut tissue pattern comprises sufficient area to repair a portion of the mitral valve; providing a first tissue forming surface and a corresponding second tissue forming surface; and, engaging the first tissue forming surface with the corresponding second tissue forming surface with the cut tissue sandwiched therebetween to form repair material to repair at least a portion of the mitral valve.

Also disclosed herein is a method of manufacturing a circulatory system valve repair element, comprising cutting harvested tissue and forming at least one leaflet from said cut tissues. The method can comprise a step of treating the harvested tissue.

Also disclosed is use of a pledget formed from a biocompatible material to reinforce the annular attachment of the repair tissue.

DESCRIPTION OF THE PREFERRED EMBODIMENTS

The subject invention is particularly suited for repair of cardiac atrio-ventricular valves (tricuspid and mitral) and cardiac outflow valves (aortic and pulmonic).

Initially discussed is a preferred method, and related instruments, for cardiac outflow valve repair. The preferred tissue trefoil pattern for use in cutting tissue for valve leaflet repair is identified with numeral 1 in FIG. 1. As shown, the pattern has three-way radial symmetry about central point 6. Shown in phantom around central point 6 is an equilateral triangle having edges 3a–c, which define the lines of coaption of the closed valve. The straight length of these edges defines the diameter of the final valve repair. For convenience herein, the term annulus is used to denote the perimeter of the orifice opening where a valve is positioned. It is known in the art that there is a range of dimensions for a particular valve; see, e.g., Sands, et al., *Ann. Thorac. Surg.* 8(5):407–14 (November 1969)) It being understood that the disclosure herein is applicable to the full range of anatomical sizes. For example, a valve annulus having a radius R requires that the length of edges 3a–c is 2R. Preferably, the pattern is used to cut tissue for repair such that the tissue lacks any seams. A seamless tissue cutting pattern, or a die incorporating the pattern, may be desirable. Use of a seamless pattern simplifies the reconstruction.

As shown, the pattern consists of three lobes, identified with numerals 10a, 10b and 10c. The outer peripheries of the three lobes is defined respectively by arcs 11a, 11b and 11c. The inner peripheries of the respective lobes are defined by arcs 2a, 2b and 2c. As shown, arcs 11a, 11b and 11c have a radius R defined in relation to the mid-points 8a, 8b and 8c of edges 3a, 3b and 3c, respectively, of the equilateral triangle. Moreover, arcs 2a, 2b and 2c have a radius R' defined in relation to points 9a, 9b and 9c. The value of R' is preferably greater than R to avoid overlapping between adjacent arcs. As will be discussed, the value of R' has no maximal value.

As previously noted, edges 3a, 3b and 3c form the lines of coaption of the closed valve. The cross-hatched areas shown in FIG. 1 define extra coaptive surfaces, the area of which is defined in relation to R'. The greater the value of R', the smaller these areas of extra-coaption. Conversely, the smaller the value of R', the greater these areas of extra-coaption.

The trefoil pattern is used to form the preferred tri-leaflet valve structure. Specifically, each lobe of the pattern will form one leaflet of the valve structure. In one embodiment, all three leaflets of a tri-leaflet valve are repaired with tissue having the trefoil pattern. Alternatively, only a portion of the trefoil pattern is employed to prepare tissue to repair a portion, generally one or more leaflets of a valve. If a full trefoil pattern repair tissue is used, in the final repaired valve, the three leaflets of the valve meet at a central coaption point. The extra-coaptive surfaces shown in cross-hatch in FIG. 1 replicate nature in that they allow for the central coaption point of the tri-leaflet valve to lie above the plane defined by the commissural points 4a, 4b and 4c.

The valve profile is a characteristic defined by the lobe length. The lobe length, as the name suggests, is the length of an individual leaflet in the tri-leaflet structure. In relation to FIG. 1, lobe length is defined as the distance between the apex of the arcs 2a, 2b or 2c, and the respective apex of arcs 11a, 11b, or 11c. In FIG. 1, these lobe lengths are identified with numerals 12a, 12b and 12c. It will be appreciated that the longer the lobe length, the higher the profile of the tri-leaflet structure, while the shorter the lobe length, the smaller the profile of the tri-leaflet structure. Because the central coaption point in the final valve will be the point at which points 8a, 8b and 8c within segments 3a, 3b and 3c intersect, a minimum value for the lobe length is R, the radius of the valve annulus. It should be appreciated that the lobe length can be varied depending on R'.

It should be appreciated that the definition of trefoil pattern described herein encompass minor variations in the size and shape of the lobes thereof which do not affect valve function, and which arise from several factors, including minor variations in the thickness of the tissue and the fact that the valve annulus is not a perfect circle.

The preferred method of repairing a semilunar heart valve using this trefoil pattern comprises the following steps:

(a) sizing an annulus of the heart;

(b) harvesting tissue;

(c) cutting the harvested tissue by use of a trefoil pattern matched to the size of the annulus;

(d) forming at least one leaflet from said cut tissue, the leaflet having a base with an outer margin of tissue extending around an outer periphery thereof; and (e) suturing the leaflet outer margin to the exposed annulus.

As appreciated by one of ordinary skill in the art, for invasive cardiac surgery additional preparatory steps for valve repair generally comprise opening the chest cavity to expose the heart, establishing the patient on cardiopulmonary bypass, and exposing the valve annulus by excising diseased valve leaflets.

The materials and methods of the invention are also suitable for use with minimally invasive cardiac procedures. In minimally invasive procedures preparatory steps can comprise placing the patient on cardiopulmonary bypass, femoral cannulation (arterial, or arterial and venous), and use of thoracoscopes and related instrumentation to visualize the valve and to facilitate repair.

Once this preparatory work has been accomplished, the next step is to size the annulus. In a preferred approach, this step is accomplished by inserting plugs of increasing size into the annulus until a plug corresponding to the size of the annulus is determined. Alternative means for sizing the valve include measurement, by use of calipers or rulers, and can also include electronic or computer-based measuring.

The next step involves harvesting tissue. It should be appreciated that a variety of tissues are possible, including autologous/autogenous tissue, allogeneic/homologous tissue, or heterologous/homogeneic tissue such as bovine tissue or porcine tissue. Moreover, many types of autologous tissue can be used, including pericardial, fascia lata, and rectus sheath (the fibrous tissue enveloping the abdominal muscles). If autologous tissue is used, pericardium is preferred, because of its proximity to the heart and the site of valve repair, and also because of its structural similarity to natural heart valve tissue. Another advantage is that pericardium has an identifiable range of thicknesses, strengths, elastin and collagen content.

The next preferred step is to treat the tissue to stiffen and/or to prevent tissue shrinkage. A preferred form of tissue treatment comprises use of glutaraldehyde, to both strengthen the tissue and to prevent it from thickening or shrinking after it has been implanted. For example, it has been found that immersion for about 10 minutes in a dilute glutaraldehyde solution, such as a 0.625% glutaraldehyde solution buffered to a pH of 7.4, produces acceptable results.

The next preferred step involves cutting the tissue. To repair a semilunar valve use of the trefoil pattern is preferred. Advantageously, a tissue cutting die comprising the trefoil pattern, matched to the size of the specific annulus involved, can be used for this purpose. Such a die can be formed from a razor sharpened blade as a cutting surface which is precisely configured to form the outline of all or part of the trefoil pattern such as that of FIG. 1, and which can be embedded in a frame of bio-compatible material, such as thermoplastic, TEFLON, polycarbonate, or polysulfone. Alternatively, a cutting instrument such as a diamond bladed knife or laser may be used along with a template having the trefoil pattern or a portion thereof.

Additional details describing the steps of exposing the valve annulus, harvesting autologous tissue from the patient, annulus sizing, tissue treatment such as with glutaraldehyde, and the use of tissue cutting dies are available in the art.

The next preferred step involves forming a tri-leaflet valve structure (or portion thereof) from the trefoil pattern (or portion thereof). The tissue is formed into a configuration which corresponds to at least a portion of a healthy valve of the type being prepared.

In a preferred embodiment, a pair of size specific formers is used. The formers of a pair are configured so that the surfaces are complementary and can engage one another. Each former comprises a tissue forming surface. When the surfaces are complementary, e.g., the convex portion of a first surface mates with a concave portion of a second surface. The surfaces need not be 100% complementary but should possess sufficient complementarity to provide the functions and results disclosed herein. The complementary tissue forming surfaces are engaged (i.e., brought into complementary engagement) while the trefoil pattern of tissue is sandwiched therebetween, in order to form the tri-leaflet valve repair structure. In one embodiment, a pair of complementary formers are manufactured into a single apparatus. Individual formers or an apparatus comprising a former can be made as disposable or as reusable. Preferably, a tissue former can comprise a region to facilitate retention of tissue thereon. For example, the tissue retention region of a former can comprise surface ridges, surface pebbling, etching, or grooves. As appreciated by one of ordinary skill in the art, any means for retaining tissue on a former is preferably configured so as to avoid trauma to any tissue placed thereon.

Figure 2A:
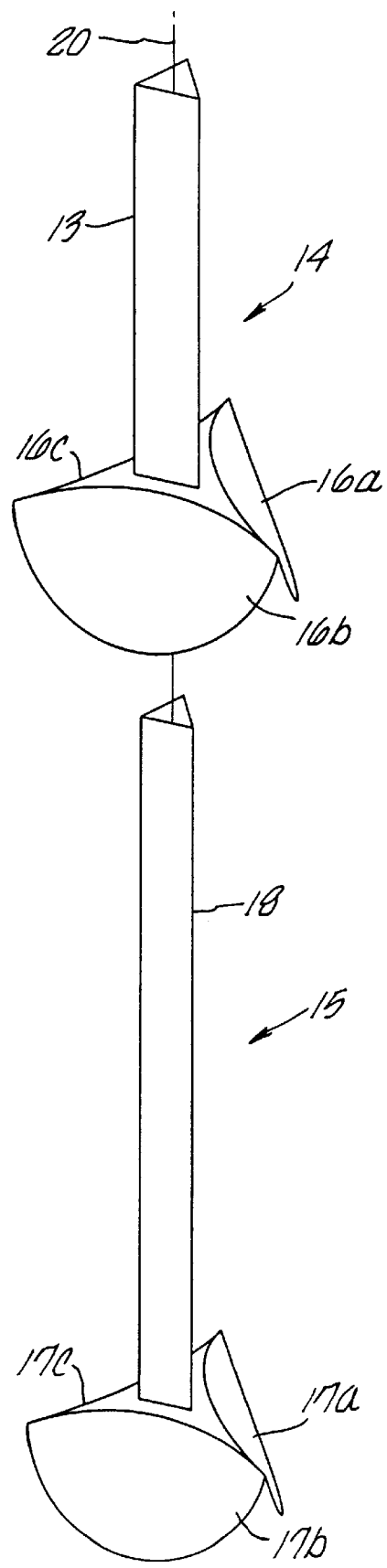
FIGS. 2a–2b illustrate oblique views of a first embodiment of upper and lower formers adapted for use in the subject invention.
Figure 2B:
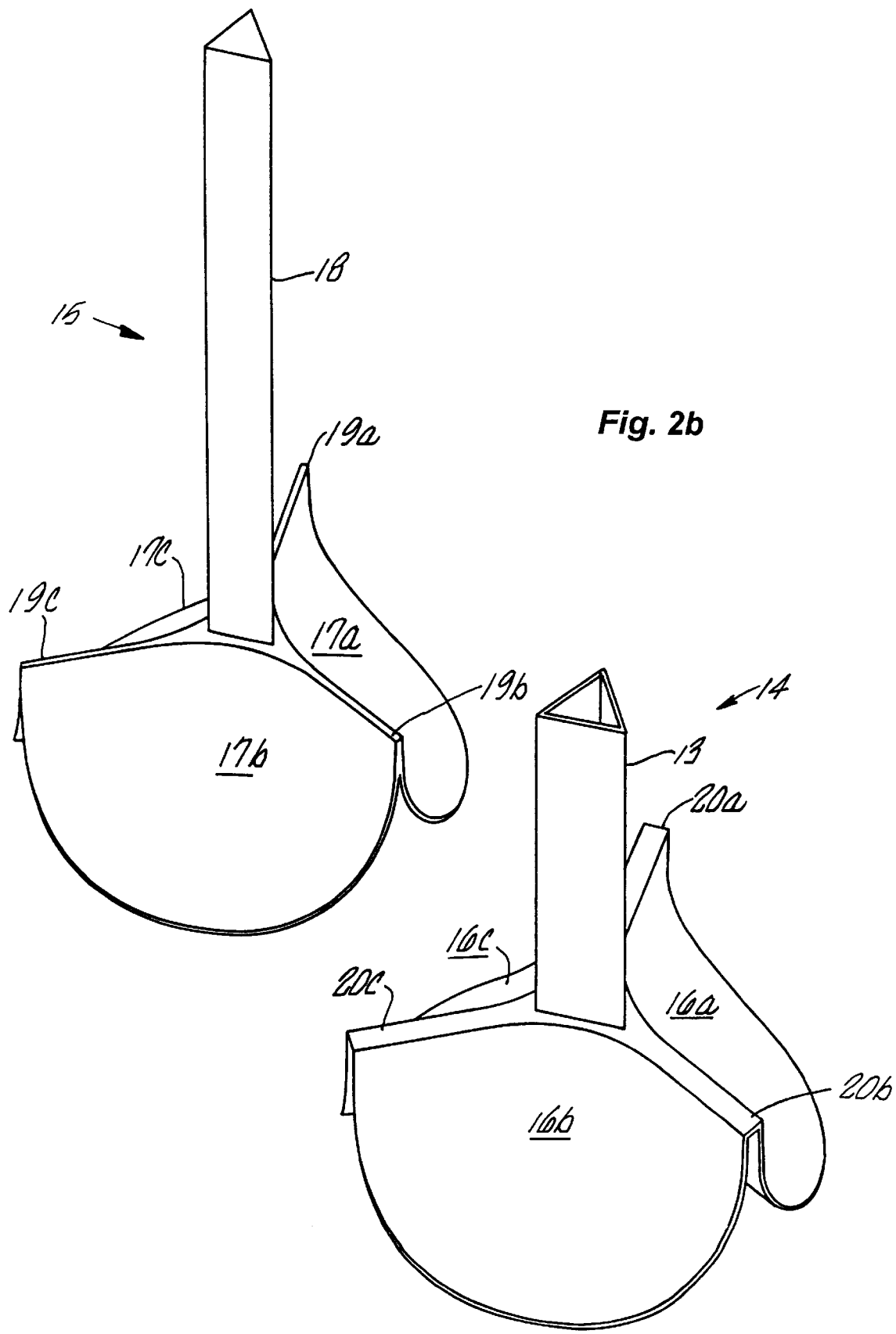

FIGS. 2a–2b illustrate preferred embodiments of the upper former 14 and lower former 15. As shown, the upper former has a handle 13 which extends along axis 20, and which in cross-section, forms a hollow polygon. Attached to one end of handle 13 are three blades, identified with numerals 16a, 16b, and 16c, which extend away from the handle in directions which are at least partially orthogonal to the axis 20 of the handle, and which are spaced about 120° from one another.

Similarly, the lower former 15 has a handle 18 which also extends along axis 20, and which, in cross-section, forms a solid or hollow polygon (FIG. 2a illustrates an embodiment in which the cross-section of the handle 18 is hollow, while FIG. 2b illustrates an embodiment in which the cross-section is solid). Attached to one end of handle 18 are three blades, 17a, 17b, and 17c, which extend from the handle in directions which are at least partially orthogonal to the axis 20 of the handle, and which are spaced about 120° from one another.

Preferably, the blades of the upper former, 16a, 16b, and 16c, and the blades of the lower former, 17a, 17b, and 17c, are molded in three dimensions to the conformation of a partially closed tri-leaflet valve as shown in FIG. 2a or FIG. 2b.

Figure 3A:
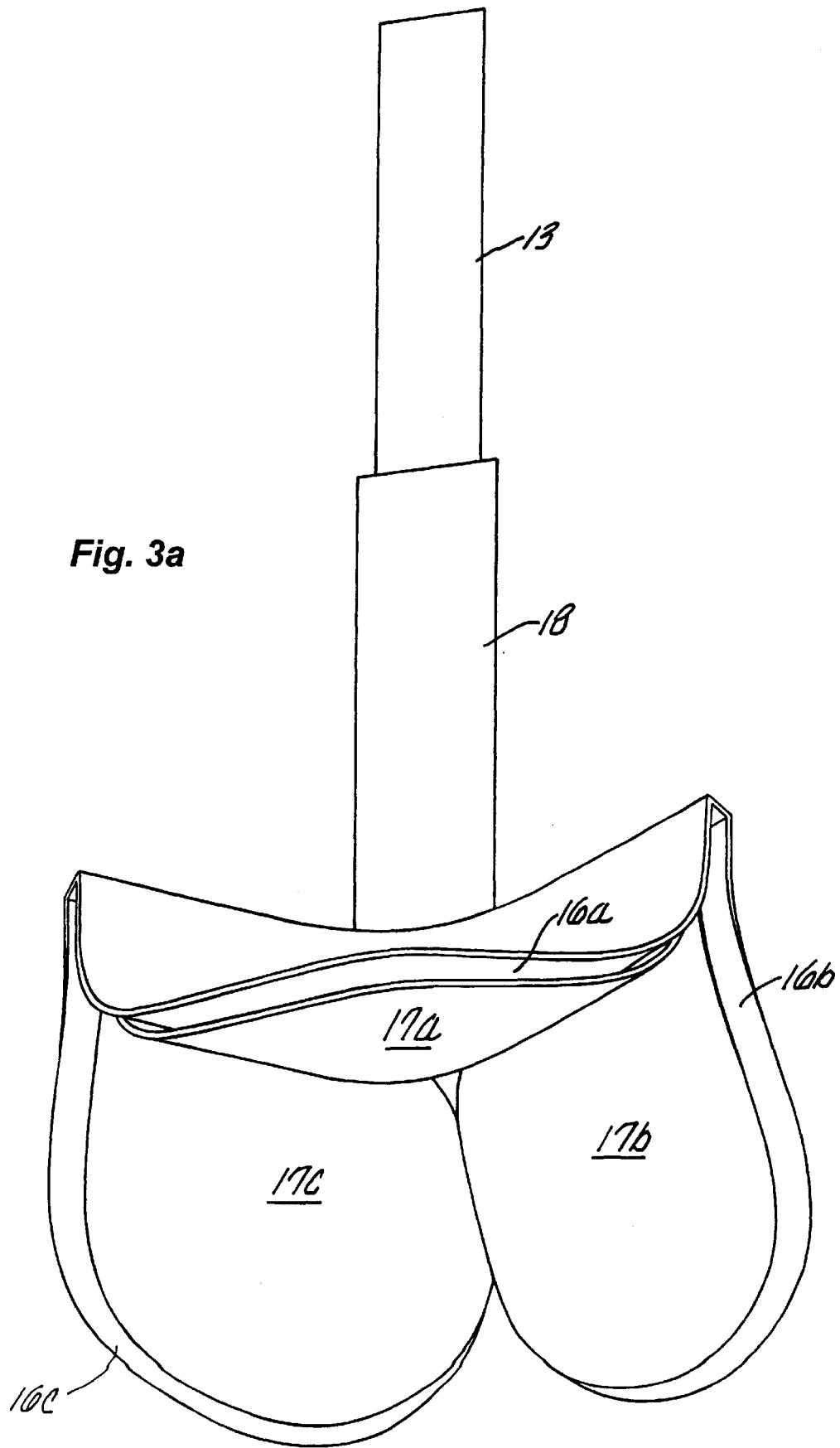
FIGS. 3a–3b illustrate oblique views from below, of the upper and lower formers of FIGS. 2a–2b.
Figure 3B:
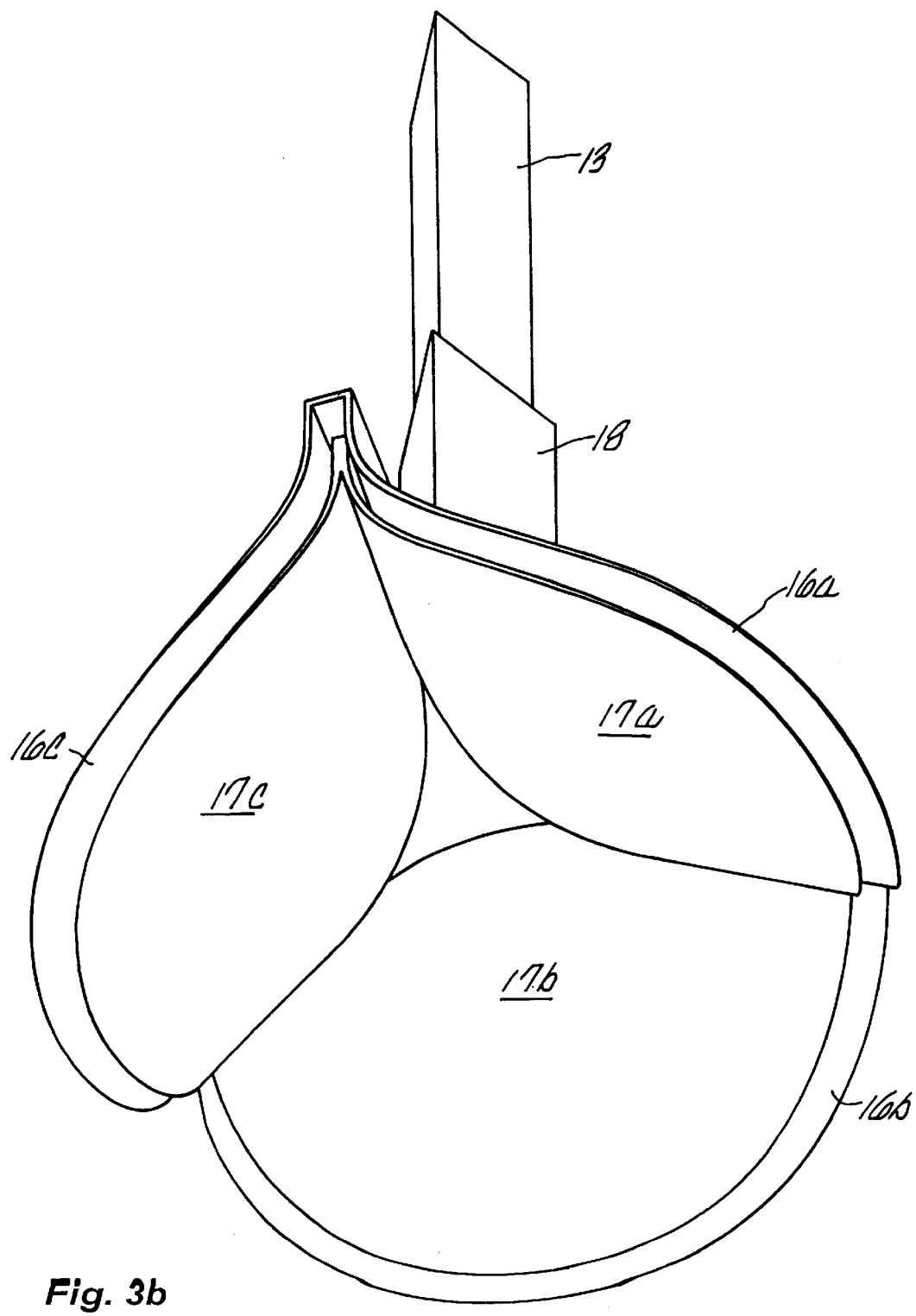

The size of the cross-section of handle 18 is preferably smaller than that of the handle 13 of the upper former, to allow handle 18 to slidably engage and be inserted into the hollow portion of handle 13, such that the blades thereof 17a, 17b and 17c can slidably engage the complementary, corresponding blades 16a, 16b, and 16c, as illustrated in FIGS. 3a–3b.

The cross-sectional shape of the handles should preferably be such as to allow for proper indexing of the formers in relation to one another. The triangular shape, such as that shown in the figures, facilitates this indexing because it prevents one handle from rotating relative to the other when the two are engaged. In general, any polygonal shape is appropriate as long as this indexing feature is provided. Handle shapes which are not polygonal in cross section are also encompassed by the invention, so long as rotation of one handle relative to the other handle is limited and preferably avoided. Moreover, complementary grooves, or complementary tabs and recesses can be provided on the handles to limit rotation of one handle relative to the other.

Figure 4A:
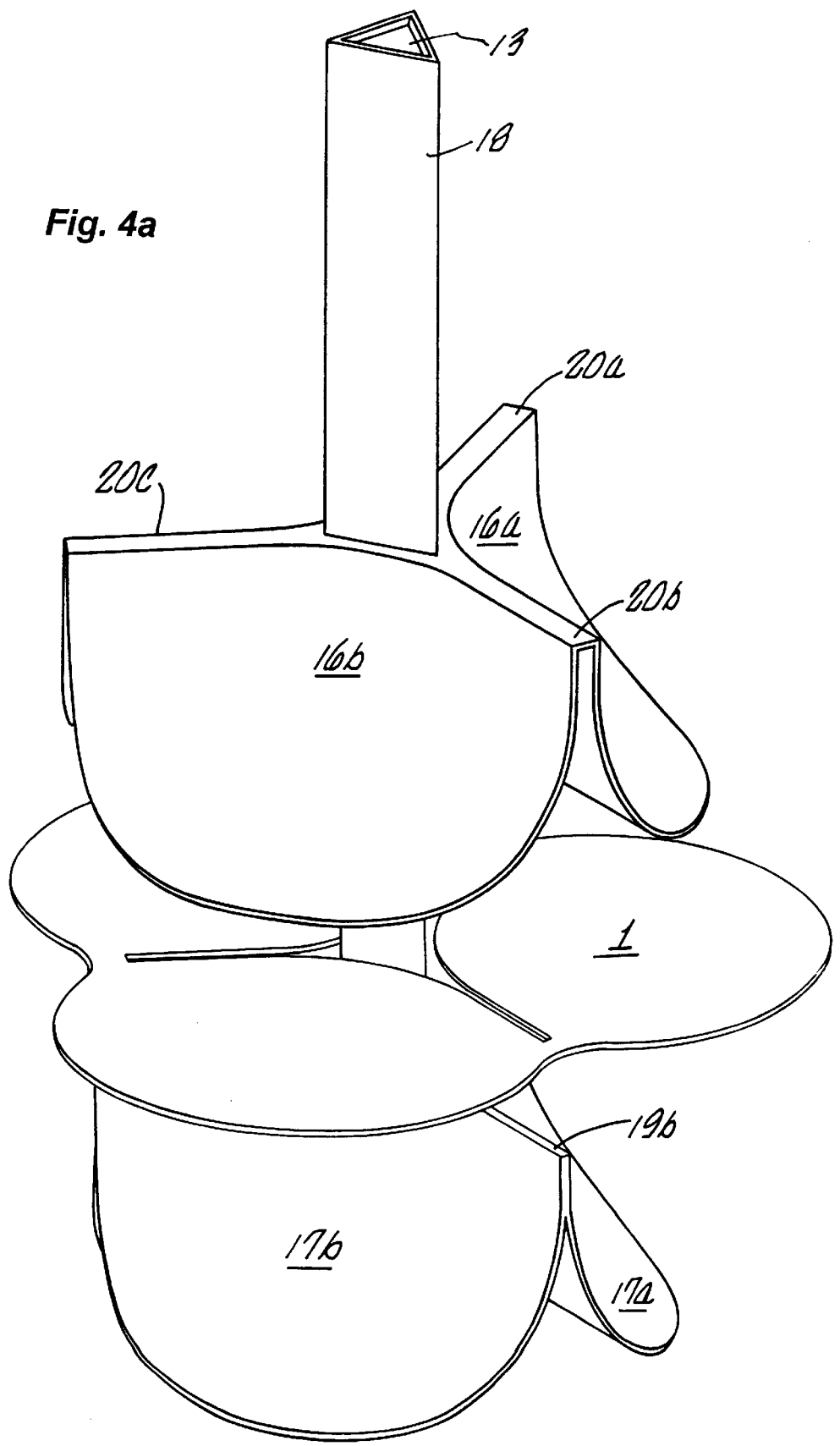
FIGS. 4a–4b illustrate partially exploded views of the upper and lower formers of FIGS. 2a–2b.

In operation, the handle 13 of the lower former is inserted through the aperture 5 of the trefoil pattern 1, and then into the hollow cross-section of the handle 18 of the upper former. The result is illustrated in FIG. 4a. The preferred complementary shape of the handles causes the blades 17a, 17b, and 17c, to be automatically aligned with the corresponding blades 16a, 16b, and 16c of the upper former. It also causes the commissural areas 19a, 19b, and 19c of the lower former to be automatically aligned with the commissural areas 20a, 20b, and 20c, of the upper former.

Figure 4B:
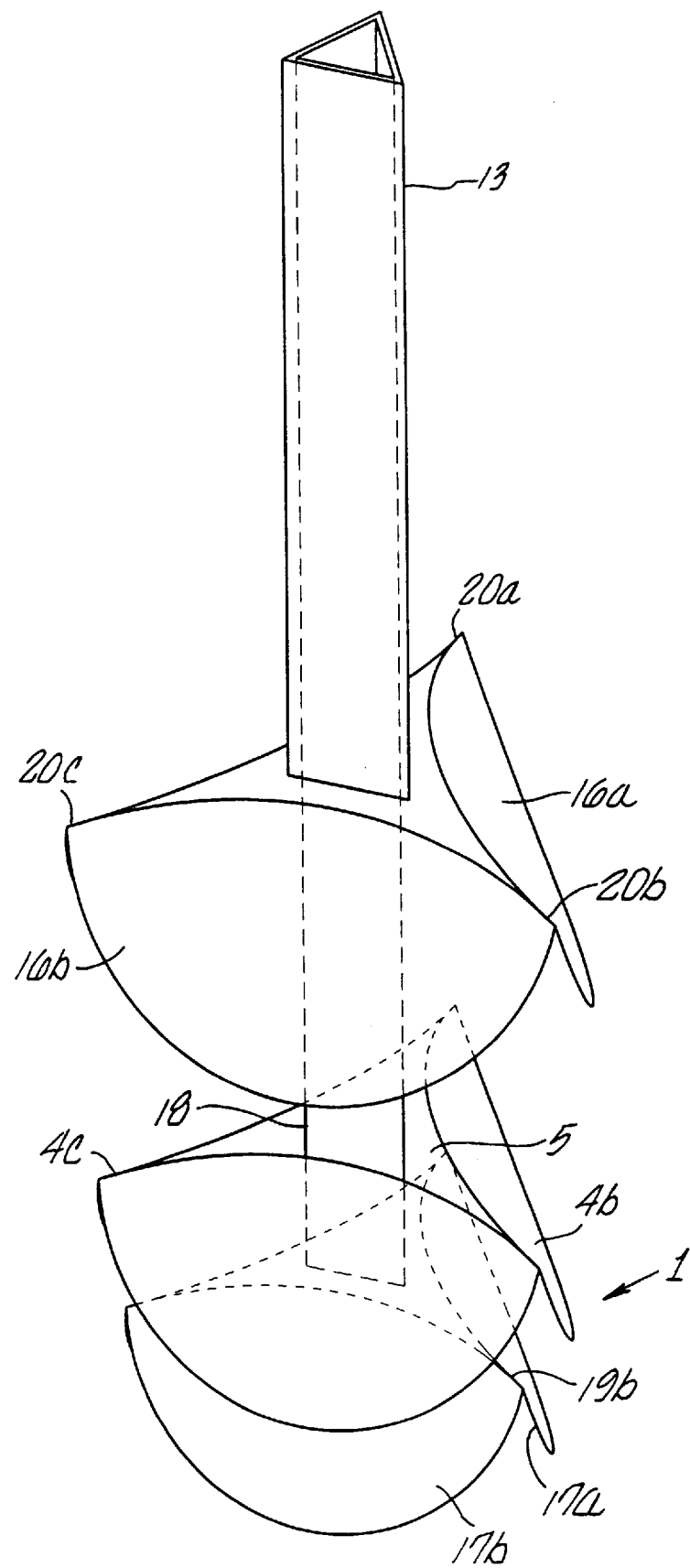

The lower former is then fully inserted into the upper former such that the trefoil pattern of tissue (or portion thereof) is sandwiched between the blades of the two formers. The blades of the two formers nest together, while the precut pattern of tissue is sandwiched between them. The result is that the cut tissue pattern is molded into the tri-leaflet structure. This scenario is illustrated in FIG. 4b.

Advantageously, the formers are constructed of a biocompatible material such as stainless steel, or plastic such as polycarbonate or acrylic. Moreover, each blade is advantageously configured to form a shape corresponding to one leaflet of the tri-leaflet valve. Accordingly, the blades are concave, and exhibit symmetry about a radial bisecting line extending from the handle through the middle of the blade.

Preferably, the blades 17a, 17b, and 17c of the lower former, and the blades 16a, 16b, 16c of the upper former, are configured to leave an exposed outer margin of tissue when the two formers have been placed in an engaging relationship with the tissue sandwiched therebetween. It has been found that a margin between 2–3 mm is most preferred. The step of suturing the valve repair structure into the exposed annulus simply involves situating the two formers with the tissue sandwiched therebetween in proximity to the exposed annulus, and then suturing the exposed strip of tissue thereto, using, e.g., either mattress sutures or continuous sutures.

For aortic or pulmonary valve repair, the line of sutures should follow a scalloped shape between commissures. After the diseased portion of the valve is excised, the repair tissue is sutured to the remnant of the valve. The geometry of the remnant (e.g., the annulus), establishes the geometry of the completed valve repair, obviating the need for a stent. Use of the annulus, which can comprise a remnant of valve tissue, is an advantageous aspect of the present invention. Suturing is done, e.g., by a continuous, distracted technique with monofilament suture that can be pulled tight after suturing, thus approximating the tissue trefoil to the valve annulus. Interrupted distracted sutures, either pledgeted or non-pledgeted, can be used in lieu of the continuous technique.

Once the suturing has been completed, the formers are withdrawn from the repair site. The upper former can be removed simply by withdrawing it from the repair site while the lower former is kept in place.

Figure 4C:
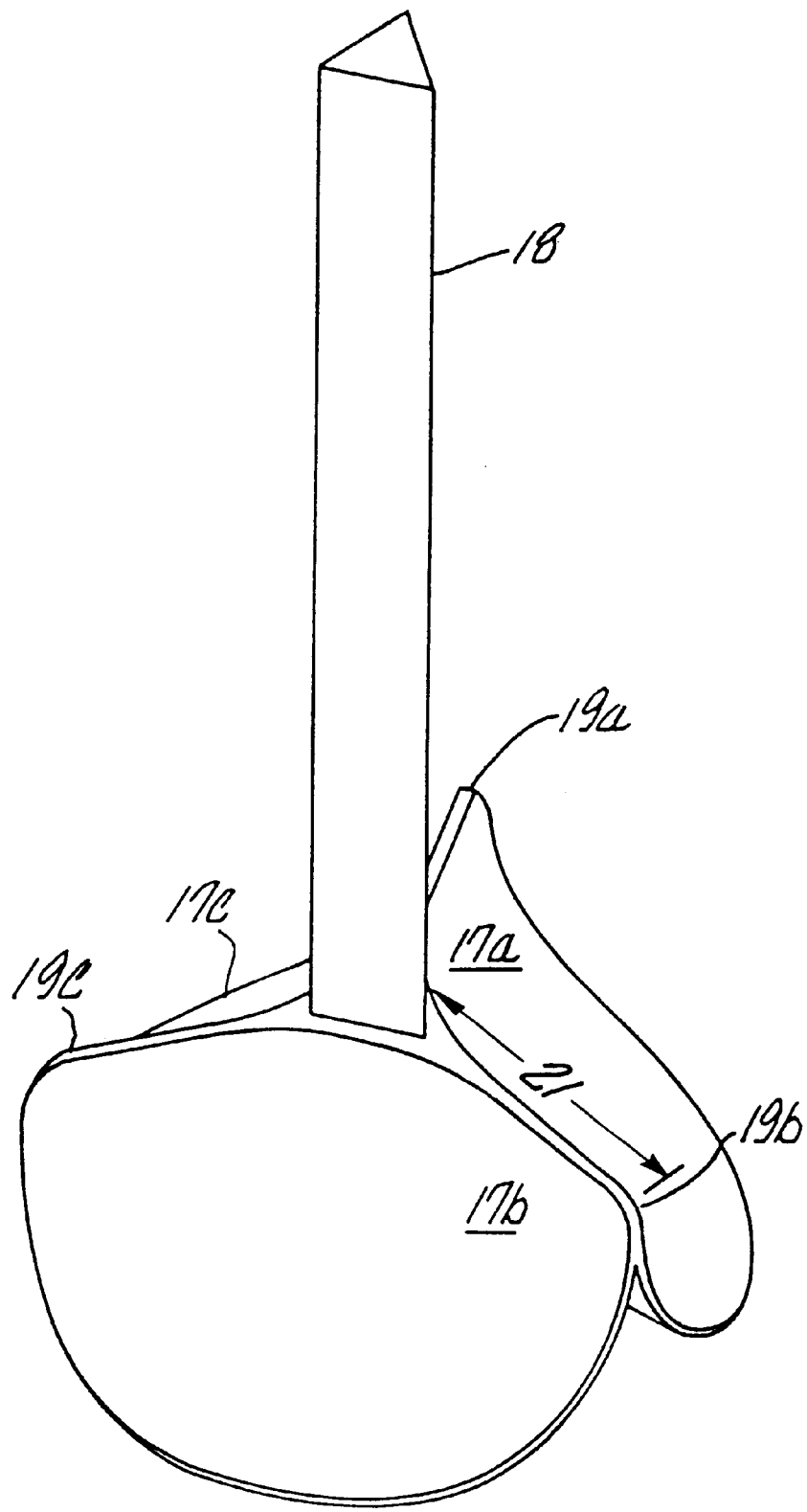
FIG. 4c illustrates an oblique view of the lower former.

To facilitate easy removal of the lower former from the repair site, the features shown in FIG. 4c can be incorporated into the lower former. Specifically, the length of the commissural lines 19a, 19b, and 19c of the lower former, which length is identified in FIG. 4c with numeral 21, should be shorter than the corresponding length of the commissural lines of the central aperture of the trefoil pattern, and the corners are rounded. That permits withdrawal of the lower former through the central orifice of the repaired valve.

Figure 4D:
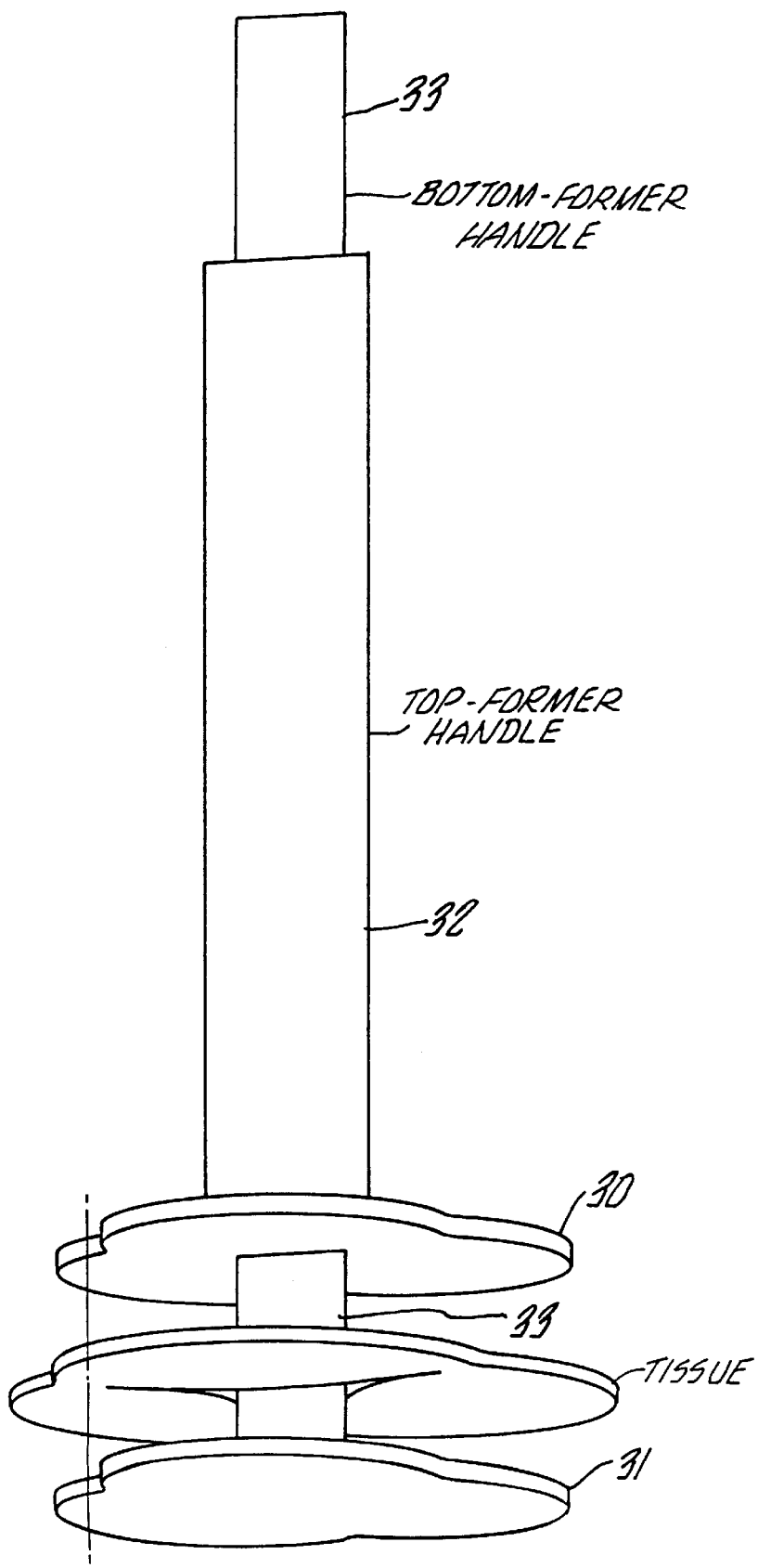
FIG. 4d illustrates a second embodiment of upper and lower formers adapted for use in the subject invention.

In a second embodiment, the forming step is performed manually by the surgeon using the apparatus illustrated in FIG. 4d. As shown, planar formers 30 and 31 are provided. Advantageously, these two formers are made of a transparent material. The tissue contacting surface of each former is configured in a two-dimensional, planar shape. The top former preferably comprises a handle 32 and bottom former 31 comprises a handle 33. Advantageously, handle 33 is slidingly received by handle 32, and these handles possess a configuration that minimizes or prevents rotation of either former relative to the other around the long axis of the interfit formers. Alternative configurations of handles 32 and 33 can comprise structures, e.g. a tab and a groove, to prevent rotation of either former relative to the other.

In the embodiment depicted in FIG. 4d, tissue in the precut trefoil pattern 1 (or a portion thereof) is sandwiched between planar formers 30 and 31. Preferably, the formers are configured to leave an exposed strip of about 2–3 mm of tissue, which is sutured to the annulus using a distracted technique, in which long loops of suture material are used to only loosely engage the strip to the annulus, and to allow the tissue to remain spaced from the annulus by about 6 inches.

When this has been accomplished, the upper former handle 32 and upper former 30 are removed. Thereafter, handle 33, and lower former 31, are removed from the repair site by pulling it through the reconstructed valve orifice.

The sutures are then tightened, thus drawing the precut tissue to the annulus. The tissue is then molded into the shape of the tri-leaflet valve simply by pressing the tissue up against the annulus remnant. The shape of the remnant thus automatically molds the tissue into the desired shape. The geometry of this remnant is illustrated in FIG. 1 of Senning A:Fascia lata replacement of aortic valves. *J Thorac Cardiovasc Surg* 54:465–470 (1967), which is hereby fully incorporated by reference herein as though set forth in full.

An additional embodiment of the invention involves the use of a size specific pre-fabricated kit, in which is contained a size specific cutting die or template for use in forming the trefoil pattern of repair tissue for the prescribed valve size, and size specific upper and lower formers configured for the specific size of the valve involved. Another variant involves use of a second non-size specific kit, in which is contained tools for harvesting tissue from the patient, a basin for tissue treatment such as with glutaraldehyde, and tools for sizing the annulus of the valve.

Figure 5A:
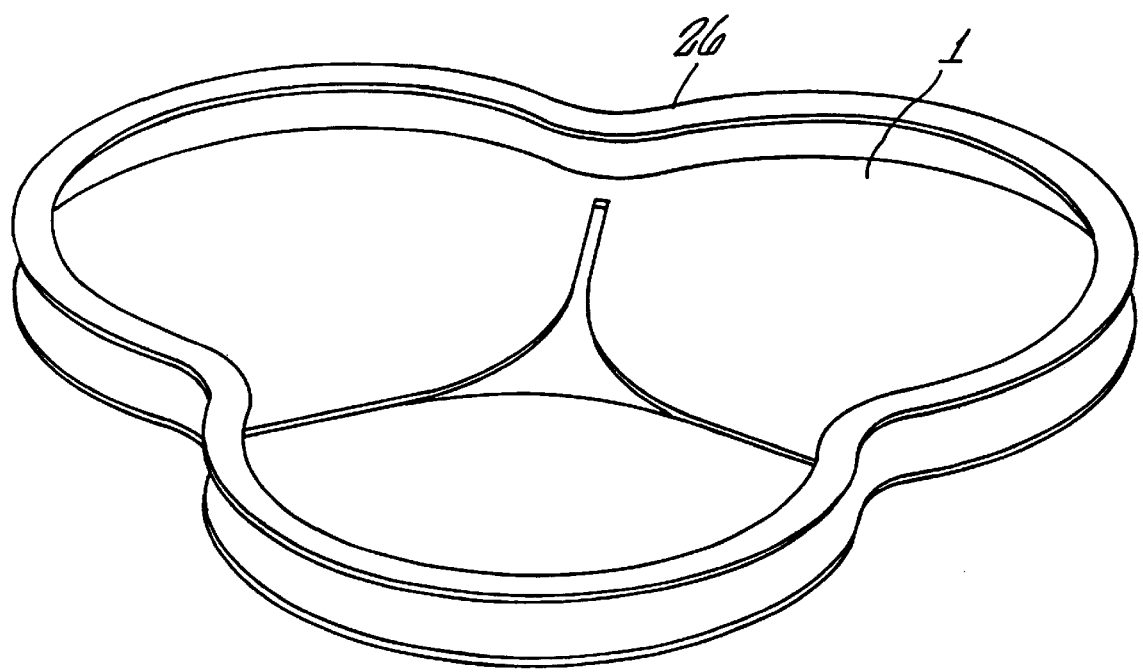

A valve reconstruction or repair, by definition, will not require a stent, but it may be desirable in some cases to add an annuloplasty ring to the reconstruction, typically of an atrioventricular valve. In those instances, the annuloplasty ring could be made a part of the annular attachment of the tissue. A further variant involves the use of a pledget for reinforcing the outer margin of tissue at the base of the tri-leaflet valve which is sutured into the exposed annulus. FIG. 5a illustrates pledget 26 and trefoil pattern 1. As shown, the pledget follows the same general outline as the trefoil pattern, and thus is specific to the size of the valve annulus. If a portion of trefoil pattern of tissue is used for valve repair, advantageously, the pledget is constructed of a flexible bio-compatible material such as thermoplastic or silicon, or a stiffened fabric such as TEFLON™ felt, DACRON™ felt, or DACRON™ velour.

Figure 5B:
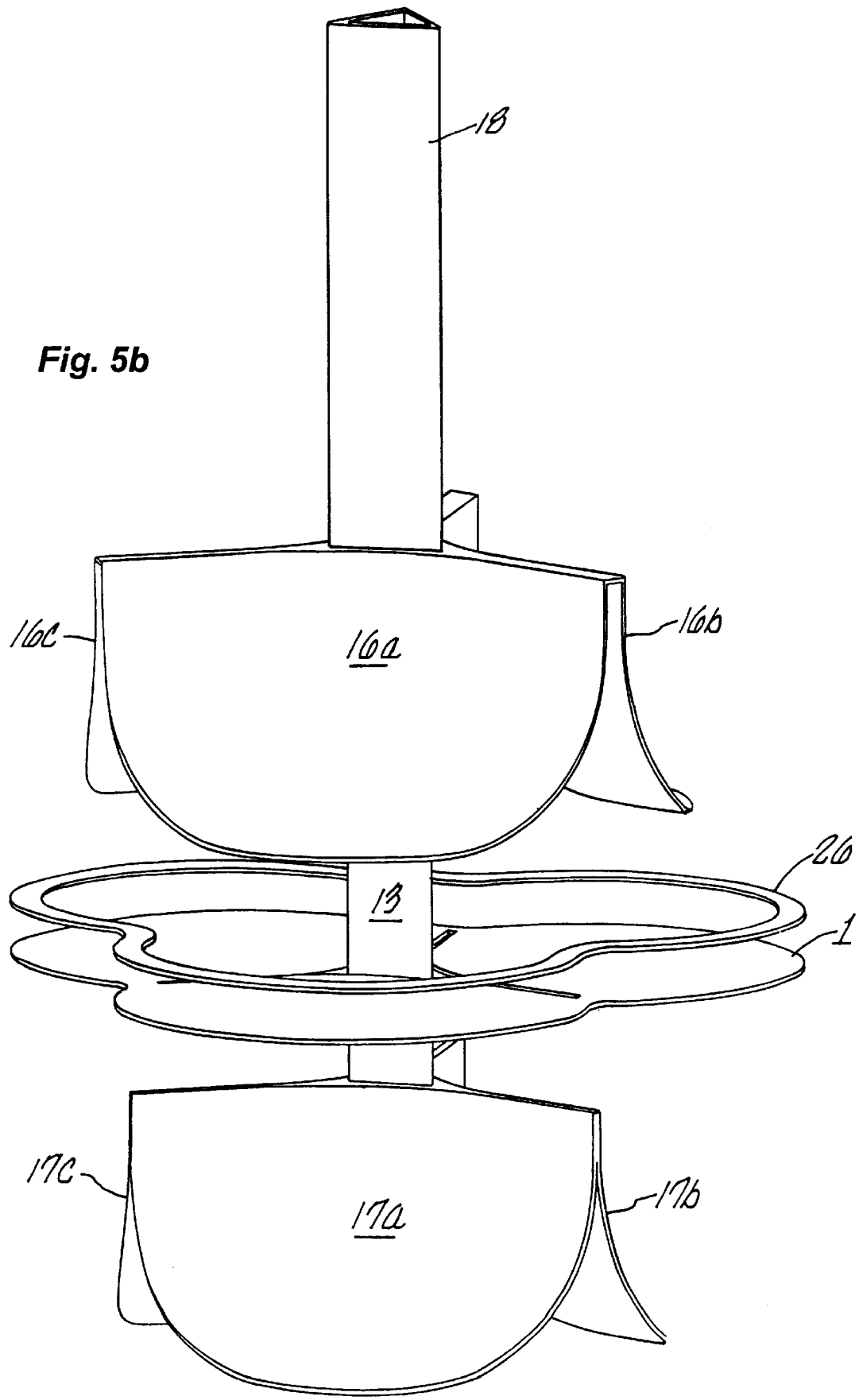
Figure 5C:
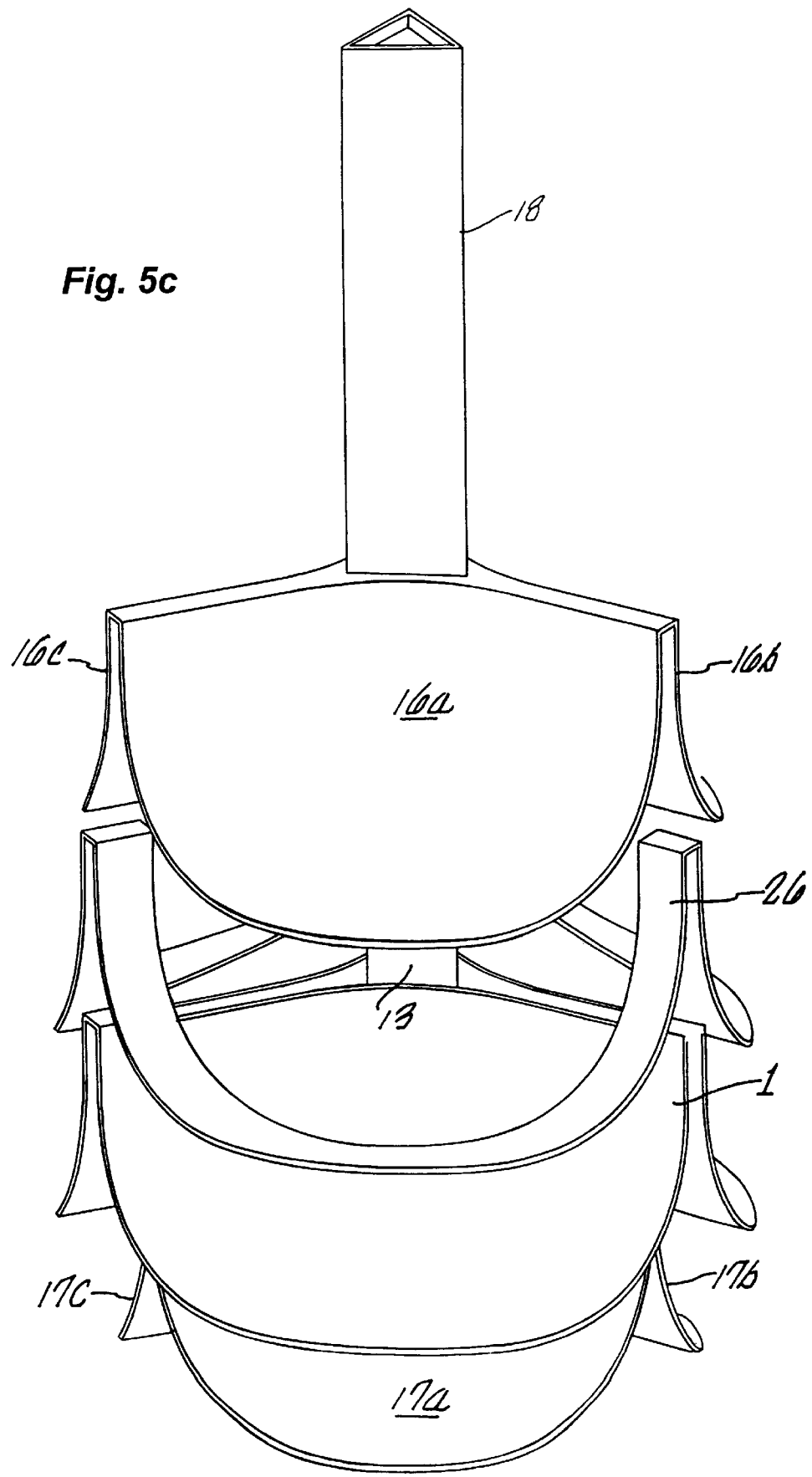

FIGS. 5b and 5c illustrate one method of utilizing pledget 26 in the context of the subject invention. As shown, pledget 26 and trefoil pattern are both inserted between the blades of the upper and lower formers in the manner described previously. Then, the lower former is fully inserted into the upper former, and the two are placed in an engaging relationship such that trefoil pattern 1 (or portion thereof) forms a valve repair structure and pledget 26 (or a portion thereof) forms a shape which matches that of the outer periphery of the base of the tri-leaflet valve structure formed from the trefoil pattern. Advantageously, the pledget 26 is at least partially situated over the edge portion extending around the outer periphery of the base of the tri-leaflet valve structure. The result is to form a reinforced edge portion. At this point, sutures are then utilized to secure the reinforced edge portion to the exposed annulus.

Another approach for utilizing a pledget in the context of the subject invention is illustrated in FIGS. 5d and 5e. As shown, the blades of the upper former are configured with a groove 27 configured for at least partial insertion of pledget 26. A side view of the groove is shown in FIG. 5e. The depth of the groove is such that the pledget protrudes at least partly beyond the edge of the former. Pins, identified with numerals 28a, 28b, and 28c, are also provided at the commissure areas 20a, 20b, and 20c of the upper former. The pledget is inserted into the groove 27 and looped over the pins 28a, 28b, and 28c. After the repaired valve has been secured in place, the pledget is disengaged from the pins, and the upper former is withdrawn from the repair site as described previously.

Turning now to presently preferred methods and structures for atrio-ventricular valve repair. Information previously discussed herein with regard to valve repair is also applicable to repair of the atrioventricular (tricuspid and mitral) valves, with presently preferred variations as disclosed. Repair of the atrioventricular valves involves, in one aspect, tissue formers that hold the tissue being used to reconstruct the valve. The formers are complementary (e.g., the convex portion of a first surface mates with a concave portion of a second surface) and function to hold at least one leaflet of the valve in a closed or partially closed position (a closed position corresponds to that of ventricular systole). In one embodiment, a pair of complementary formers are manufactured into a single apparatus; in an alternative embodiment two pair of complementary formers (e.g., a pair for each leaflet)are manufactured into a single apparatus.

Due to the configuration of the atrioventricular valves as compared to the semilunar cardiac outflow valves (aortic and pulmonary valves) modifications are made to the devices and methods used when repairing these respective circulatory system valves. Unlike the semilunar valves, in which each leaflet has essentially the same geometry, each leaflet of an individual atrioventricular valve is generally not uniform. For example, the anterior leaflet of the bicuspid valve is much larger than that of the posterior leaflet.

A preferred embodiment of the invention comprises repair of two leaflets of a valve; this results in repair of each leaflet or a bicuspid valve, and repair of two-of-three of the leaflets of a tricuspid valve or repair of a tricuspid valve such that it is remodeled into a bicuspid configuration. The presently preferred two leaflet repair of a tricuspid valve is chosen for several reasons, on the right side of the heart there are additional points of attachment to the valve to the interventricular septum; these attachments are very difficult to duplicate in a repair procedure. Another basis for this choice of tricuspid repair is that this valve is relatively less important for good cardiac function than is the critically important mitral valve, and modifications of its structure are also less critical.

There are two papillary muscles in each ventricle that function to anchor the leaflet free edges by way of the chordae tendineae. It is believed to be advantageous to use bicuspid geometry for either atrioventricular valves, with the leaflets anchored to the papillary muscles. Alternatively, the tricuspid configuration can be modeled, whereby tricuspid formers in accordance with the invention are used.

Figure 6A:
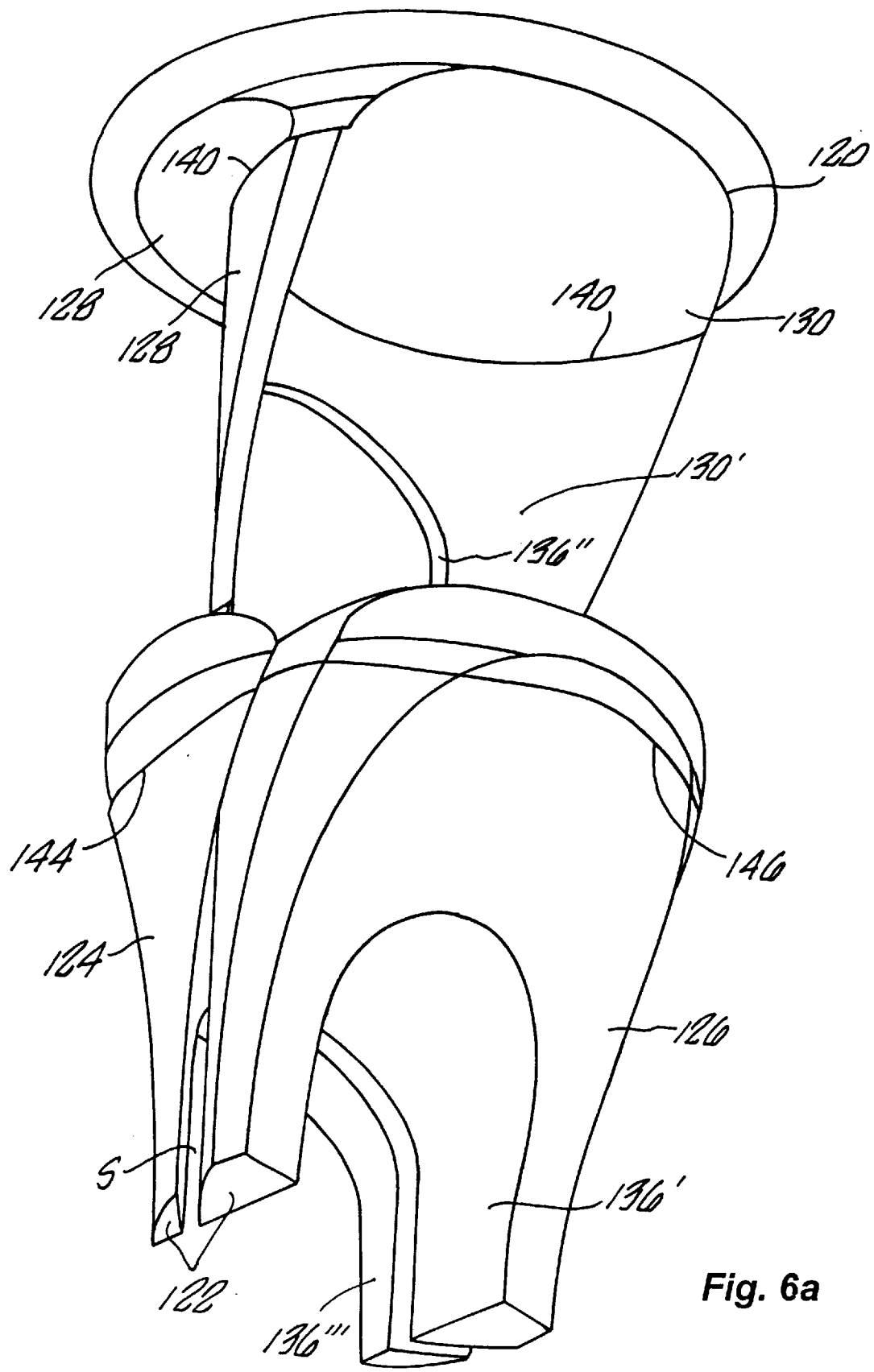
FIGS. 6a–6c illustrate three different perspective views of formers for atrioventricular valve repair material.
Figure 6B:
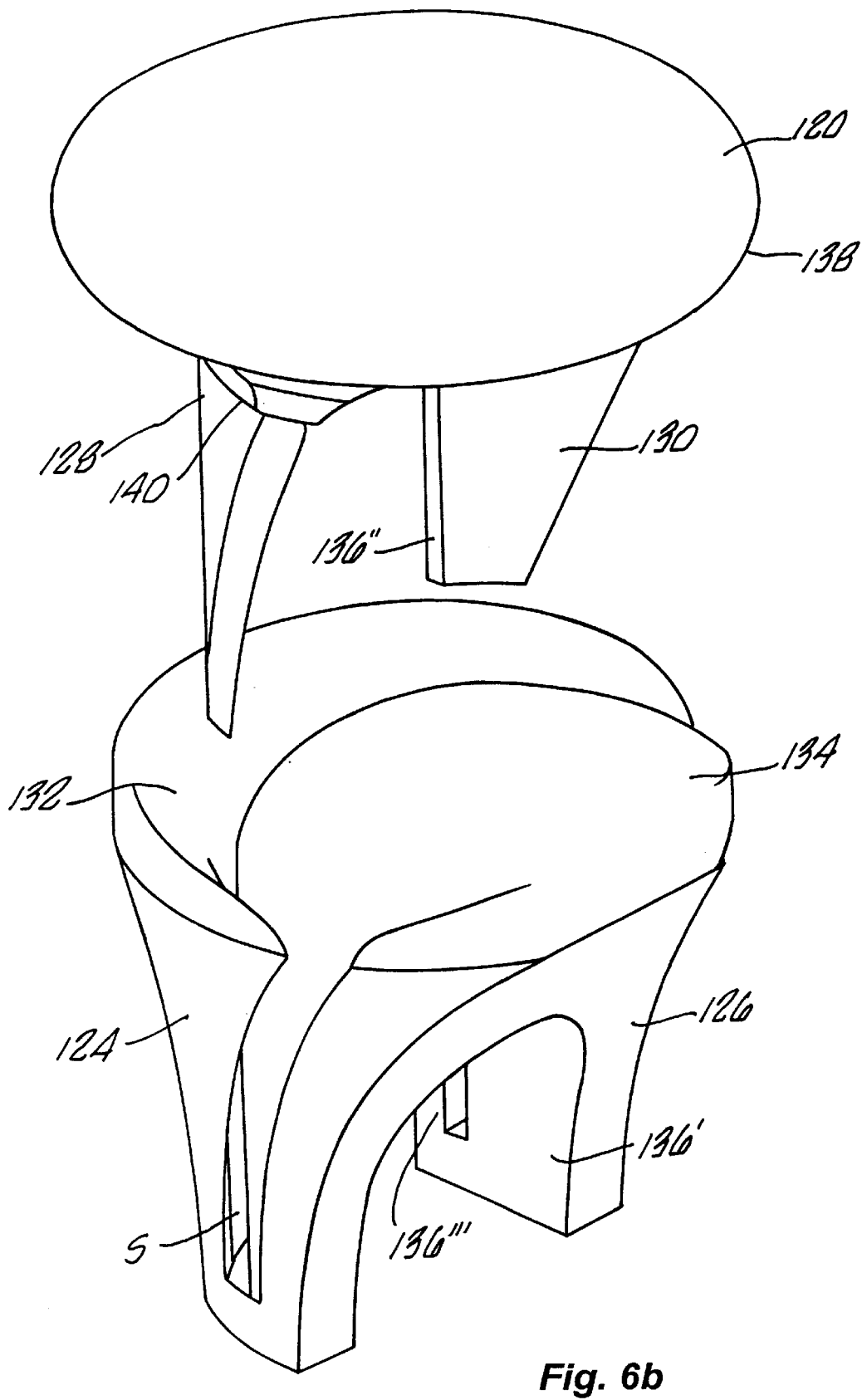

As with the semilunar valve repair, a sheet of tissue is sandwiched between the atrioventricular valve formers so the tissue is presented to the surgeon in the geometry of a closed bicuspid valve, as shown by FIGS. 6a–b.

In some repairs or reconstructions the chordae tendineae may still be useful. For such repair/reconstructions it is desirable to leave the chordae intact, generally along with a contiguous leaflet free edge to which valve-repair material can be sutured. For these repairs, the physician need not create chordal extensions on the new leaflets or create pseudo chords. The materials and methods herein thus provide the surgeon with greater flexibility when planning and executing a procedure.

As depicted in FIGS. 6a–b, the formers for use in creating repair leaflets for a mitral valve are unique based on the asymmetry of the leaflets that make up this valve. The geometry of these leaflets will be discussed in the context of how the tissue forming surfaces are configured. It being understood that complementary formers are configured so that tissue formed by use of these formers possess a configuration of at least a portion of a healthy valve. For example, one can prepare an array of formers by producing pairs that correspond to an array of healthy anatomical specimens; preferably human specimens are used, however due to interspecies anatomical similarities, it is also acceptable to use nonhuman specimens.

The geometry for the larger, anterior leaflet of the mitral valve is relatively straightforward, a convexo-concave surface with extensions for anchoring to the anterior and posterior papillary muscles. The anchoring extensions function as the chordae tendineae. The extensions can be fabricated by providing intact tissue as a portion of a valve leaflet, or by cutting pseudo chords by excising teardrop segments from the extensions by use of a tissue cutting pattern such as that shown in FIG. 10.

The geometry of the smaller but longer posterior leaflet is less straightforward because in the closed position it is more notably different than a simple convexo-concave surface. The posterior leaflet occupies about 220°–240° of the annular circumference. In the closed position, the geometry is best likened to a partial toroidal section. A toroid is a form that corresponds to that of an ovoid, when the ovoid is rotated about a point which is not within a plane of the ovoid. Thus, a toroid has two different curvatures. A common example of a toroid is a doughnut shape. The two different curvatures of the posterior leaflet of the mitral valve are the curve of the valve annulus in one plane and the additional curve of the closed leaflet, which exists in all planes through the leaflet perpendicular to the annular plane. The posterior leaflet of the mitral valve is not a complete toroid because it is comprised of only a portion of a toroidal ring shape, a portion that is approximately one-fourth of the toroid. This double curvature imposes a need for some elasticity that will accommodate to the two curves, and correlates to a preferred variation between tissue preparation for semilunar valve reconstruction and atrioventricular valve reconstruction. The difference is that the tissue is preferably treated with brief immersion in a treating solution to reduce shrinkage and/or to stiffen tissue before mounting on the formers for semilunar repair, but after mounting on the formers in the atrioventricular valve repair. A presently preferred treating solution comprises glutaraldehyde. The pericardium is more pliable and slippery to handle, and is more elastic before it is exposed to glutaraldehyde. The objective of the preferred embodiment is to mold the geometry and to preserve it with, e.g., the glutaraldehyde immersion to make the tissue stiffer. Since there is a degree of shrinkage when the tissue is immersed in glutaraldehyde, in atrioventricular valve repair it is preferred that the tissue is not cut until after it is molded and then treated with glutaraldehyde. After the glutaraldehyde treatment, the two layers of tissue forming the leaflets are trimmed with a knife, preferable a diamond knife, and scissors, to establish the final shapes of the two bicuspid leaflets. As depicted on FIGS. 6a–b, the chordal extension legs of the two formers are removable/detachable so they will not damage the ventricular wall. Alternatively, the formers are constructed such that the chordal extension legs are retractable, by use of mechanisms known to those of ordinary skill in the art. The outer margin of the two leaflets are sutured to the valve annulus, the formers are removed, and the chordal extensions are attached to the papillary muscles. The papillary muscle attachments are preferably made with pledgeted non-absorbable sutures in standard fashion.

Figure 6C:
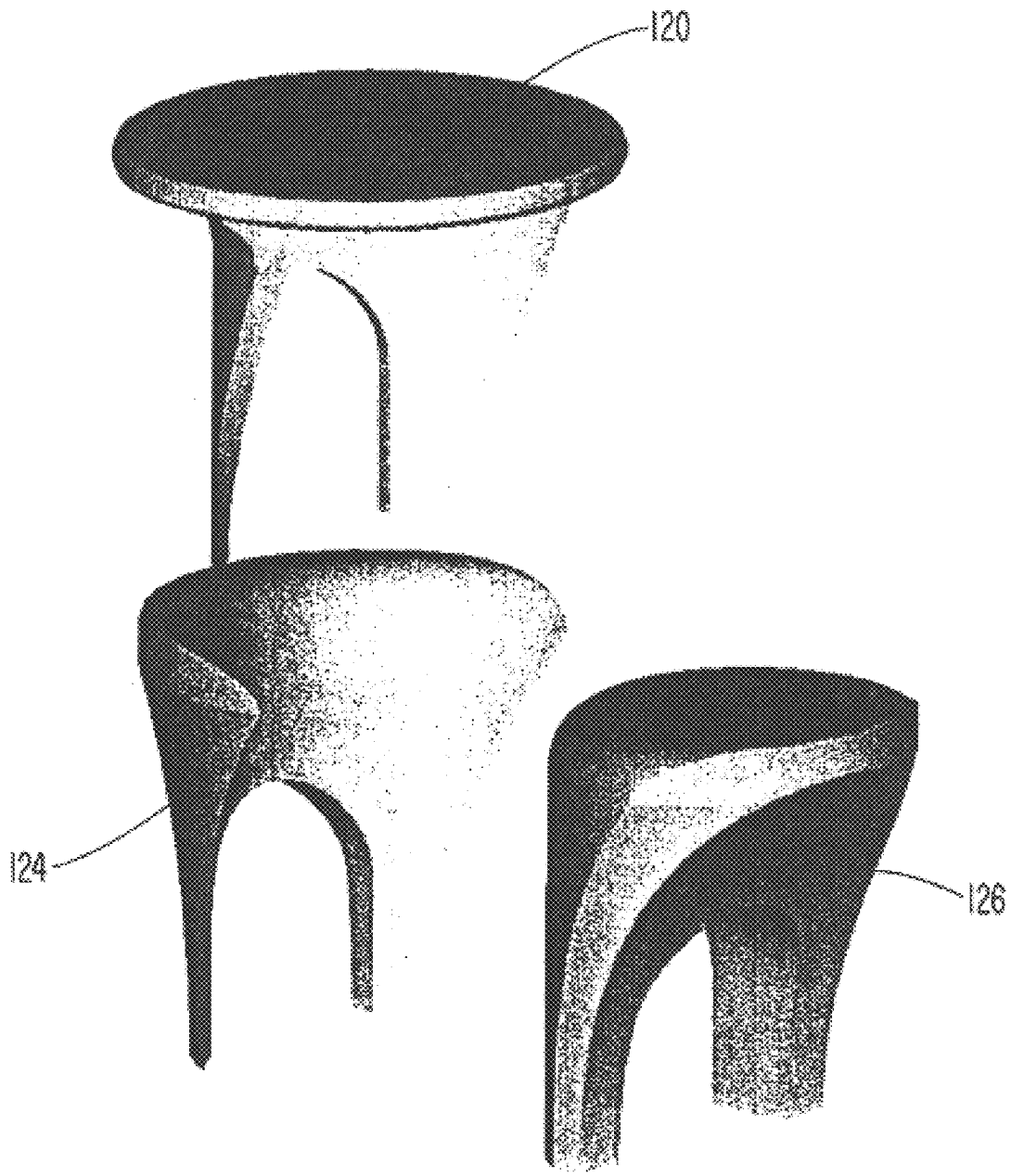

FIGS. 6a–c illustrate three different oblique views of an embodiment of atrioventricular formers in accordance with the invention. For explanatory purposes only, the forming instrument will be referred to as comprising an upper former 120 and a lower former 122. Lower former 122 comprises a posterior leaflet former 124 and an anterior leaflet former 126. Not illustrated in FIG. 6a and FIG. 6c is an optional connection between posterior leaflet former 124 and anterior leaflet former 126; the optional connection is depicted in FIG. 6b. For the variant of embodiment (e.g., FIG. 6A and FIG. 6c) that has separate lower formers for each leaflet, an upper former can be used that comprises surfaces complementary to each lower form, this is presently preferred for economy of manufacture. Alternatively an upper former having only a forming surface complementary to an anterior leaflet, or an upper former having a only a forming surface complementary to a posterior leaflet are within the scope of the invention. The embodiment of upper former 120 depicted in FIGS. 6a–c comprises two tissue forming surfaces, a posterior leaflet forming surface 128 and an anterior leaflet forming surface 130. Advantageously, forming surfaces in accordance with the invention preferably comprise a n area to form chordal extensions, e.g., surface 130' in FIG. 6a. Posterior leaflet former 124 of the lower former comprises a tissue forming surface 132, and anterior leaflet former 126 of the lower former comprises a tissue forming surface 134.

As depicted in FIG. 6a and FIG. 6b, posterior leaflet forming surface 128 of upper former 120 is complementary to and engagable with posterior leaflet forming surface 132 of posterior leaflet former 124; anterior leaflet forming surface 130 of upper former 120 is complementary to and engagable with anterior leaflet forming surface 134 of anterior leaflet former 126.

In use of the embodiment of a forming instrument as depicted in FIG. 6, a single piece of tissue is folded in a "V" configuration, and the apex of the folded tissue is inserted into space S which is the limited by posterior leaflet former 124 and anterior leaflet former 126. Thereafter, upper former 120 is inserted into the "V" between the two portions folded tissue, such that a sandwich configuration occurs of: a lower former, a tissue layer, upper former, a tissue layer, and, a lower former.

In a preferred embodiment of a method in accordance with the invention, the tissue is then subjected to treatment, such as glutaraldehyde, so as to stiffen the tissue and/or to minimize tissue shrinkage and thickening. Generally following the tissue treatment step, an orifice for the valve is incised along margin 136. Margin 136 is comprised of three components, margin 136' of lower anterior leaflet former 126, margin 136" of upper former 120 and margin 136'" of lower posterior leaflet former 124.

Excess tissue extending laterally beyond the upper and lower formers is incised. Advantageously, the perimeter 138 of upper former 120 serves as a margin along which any excess tissue can be cut. Preferably, perimeter 138 has a configuration that corresponds to the annulus of the valve being repaired. For example, size specific formers will, therefore, comprise various sizes, where for each size the forming surfaces are configured to correspond to the annulus being repaired , and perimeter 138 is also configured to correspond to the annulus being repaired.

The valve repair material held by the formers can then be sutured to the annulus in accordance with standard surgical procedures. The chordal extensions of tissue are sutured to their respective papillary muscles or residual chordae tendineae.

The upper and lower formers can then be removed from the patient. Preferably, to facilitate removal, upper former 120 comprises a detachment point 140. Preferably the portions of upper former 140 which provide for preparation of chordal repair material are detachable at point 140 or are articulated at this point, whereby upper former 120 and its detached or articulated chordal forming portions, e.g., 130" in FIG. 6a, are retracted through the newly formed valve orifice. Alternatively, lower posterior leaflet former 124 comprises a point of detachment or articulation 144 so as to facilitate movement of components of the lower former through a newly formed valve orifice. Alternatively, lower anterior leaflet former 126 comprises a point of detachment or articulation 146, so as to facilitate movement of components of the lower former through a newly formed valve orifice.

The embodiment of the formers depicted in FIG. 6a and FIG. 6a comprises the ability to form anterior and posterior atrioventricular valve leaflets from a single piece of repair tissue. It is also within the scope of the invention that an upper former comprising a posterior leaflet forming surface, but not an anterior leaflet forming surface, has a tissue forming surface that is complementary to and engagable with a posterior leaflet forming surface of a lower former, the lower former lacking an anterior leaflet forming surface. Moreover, it is within the scope of the invention that an upper former comprising an anterior leaflet forming surface, but not a posterior leaflet forming surface, comprises a tissue forming surface which is complementary to and engagable with an anterior leaflet forming surface of a lower former, where the lower former lacks a posterior leaflet forming surface.

Thus, two alternative approaches to atrioventricular leaflet molding are also presently preferred. One alternative is to mold each leaflet from a separate piece of tissue, in which case there are two forming surfaces for each leaflet, thus a total of four surfaces for each bicuspid valve. An alternative, discussed above, is to mold the leaflets by inserting a folded piece of tissue between the two forming surfaces of a first forming instrument, and then to insert a second forming instrument between the two leaflets. The second forming instrument is complementary to and mates with the first forming instrument.

Furthermore, the general shape of the anterior and posterior leaflets with chordal extensions is shown, e.g., in FIGS. 7a–c, FIG. 8 and FIG. 10.

Thus, further embodiments of configurations for valve repair material in accordance with the invention are illustrated in FIGS. 7a–c, FIG. 8 and FIG. 9. FIG. 7a depicts a tissue cutting pattern capable of use to cut tissue to be used for repair of an atrioventricular valve. Advantageously, the pattern depicted in FIG. 7a permits a single flat piece of tissue to be formed into repair material for an atrioventricular valve. The pattern comprises extensions 150. When repair material is cut using this tissue cutting pattern, the repair material defined by extensions 150 is useful to repair the chordal extensions.

FIG. 7b depicts a piece of repair material cut according to the pattern of FIG. 7a. The orifice of the valve repair material is created by making an incision along line 152 of FIG. 7a. FIG. 7c depicts a finished cylindrical shape for a valve repair material, preferably comprising chordal extensions, prepared by use of a pattern of FIG. 7a. As appreciated by one of ordinary skill, the pattern of FIG. 7a may be comprised by the cutting edge of a tissue cutting dye, or by a margin of a tissue cutting template. As depicted in FIG. 7a, the modifications of the pattern which provide for extensions 150 are along the short edges of the generally rectangular pattern.

Figure 8:
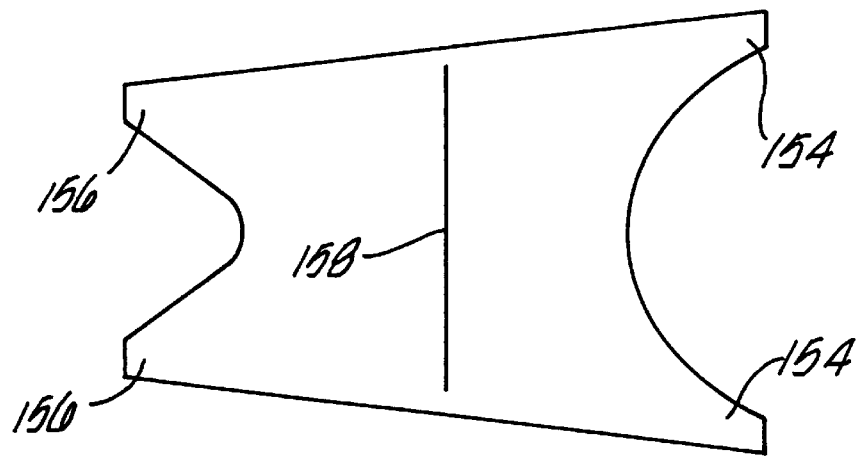
FIG. 8 is a trapezoidal pattern to produce larger anterior and smaller posterior leaflets, and asymmetrical papillary muscle attachments. This pattern is preferred as it more closely corresponds to normal healthy anatomy.

FIG. 8 depicts an alternative embodiment of a pattern for use to create repair material for an atrioventricular valve. FIG. 8 comprises a bilaterally symmetrical trapezoid. The configuration of this embodiment is designed to produce larger anterior and smaller posterior leaflets, and asymmetrical capillary muscle attachments, so as to more closely correspond to normal anatomy. The pattern of FIG. 8 encompasses extensions 154 and extensions 156. When tissue is cut according to this pattern, the tissue areas delimited by extensions 154 and 156 are useful for repair of the chordal apparatus. To create the orifice of the repaired valve, an incision is made along line 158. Optionally, additional tissue may be removed adjacent to the incision to modify the valve opening. Alternatively, the incision may be made along a curve to provide for effective valve function.

Figure 9:
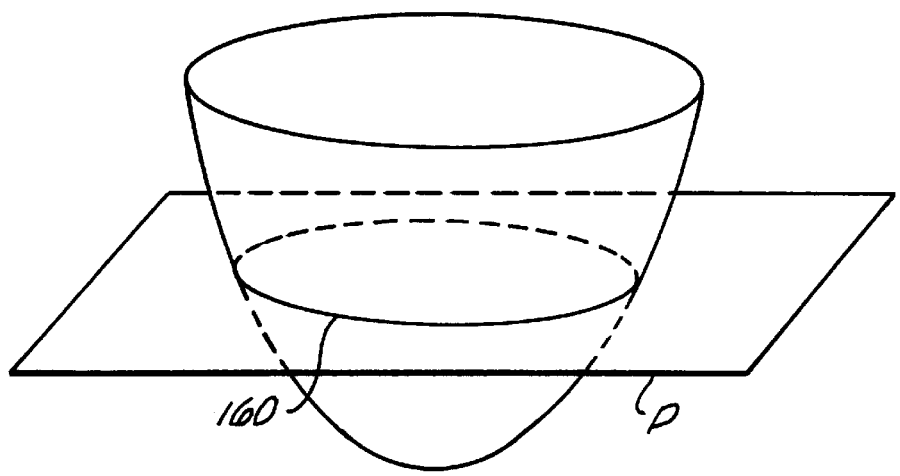
FIG. 9 depicts the use of a solid tissue parabola from nature, the apical portion of a pericardium. An apical cap of pericardium, human or animal, is harvested, then transected. The plane of section of the parabolically shaped tissue is selected to match the size of a valve annulus. Papillary muscle attachment legs can be fashioned from either flared tissue above or apical tissue below the plane depicted in FIG. 9. Turning the entire piece of tissue inside out produces a concave shape to the leaflets; this is presently preferred as more closely corresponding to healthy anatomy.

FIG. 9 depicts a parabolic shape, such as is available by harvesting pericardium from a heart apex. As in other embodiments of the present invention, the harvested tissue may be autologous, homologous or heterologous. A plane of section, P, is selected so as to provide an opening/orifice 160 of the valve being prepared. As appreciated by one of ordinary skill in the art, chordal mechanisms can be incised from the pericardial tissue. The chordal extensions can be cut from the portion of the pericardium in FIG. 9 depicted above plane P, whereby portions of the pericardium above the plane comprise the valve repair material. Alternatively, the chordal extensions can be incised from portions of the pericardium depicted below plane P in FIG. 9, whereby the apical portion of the pericardium comprises the valve repair material. Advantageously, by use of parabolic shaped pericardial tissue, the tissue can be turned inside out which produces a concave shape to the leaflets, i.e., the leaflets are curved inward toward the valve orifice.

Figure 10:
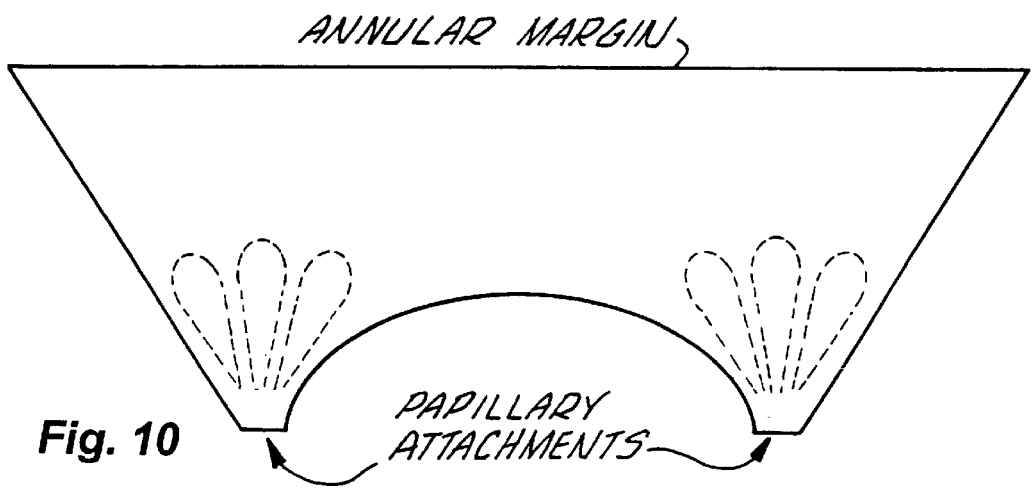
FIG. 10 depicts a pattern for tissue cutting that is used to create material for atrioventricular valve repair. When the pattern is used to cut tissue, pseudo-chordae tendineae are created.

FIG. 10 depicts the preparation of pseudo chordae tendineae. The pseudo chordae tendineae can be prepared from any chordal extension of the invention. Pseudo chordae tendineae are prepared by incising tissue in a "tear drop" shape as depicted in FIG. 10. It can be advantageous to prepare pseudo chordae tendineae, as incision of tissue along the dotted lines in FIG. 10 produces removal of unnecessary tissue and permits more blood to flow through the heart valve orifice.

While embodiments and applications of this invention have been shown and described, it should be apparent to those of ordinary skill in the art that the these examples are merely illustrative, and that many embodiments are possible without departing from the spirit and scope of the subject invention. Specifically, it should be appreciated that the subject invention can be used to repair less than all, i.e., one or two, leaflets of a diseased valve. The process would involve forming a precut pattern comprising only one or two of the lobes/segments shown in FIG. 1, and using the resultant tissue to repair the valve in the manner described, except that only the one or two prescribed leaflets in the native valve would be excised and repaired. Accordingly, the invention is not to be restricted, except as by the appended claims.

What is claimed is:

1. A surgical instrument for holding a piece of tissue in a configuration of at least one leaflet of a circulatory system valve to facilitate surgical attachment of the tissue, the instrument comprising:

a. a first and second former having respective first and second tissue forming surfaces, wherein the first tissue forming surface is complementary and engagable to the second tissue forming surface, such that when tissue is placed between the first tissue forming surface and the second tissue forming surface, and the tissue forming surfaces are brought into complementary engagement, the tissue is held in a configuration of at least one leaflet of a closed or partially closed circulatory system valve; and b. a first handle attached to the first former and a second handle attached to the second former for holding the tissue forming surfaces in complementary engagement, whereby the tissue may be held in place for surgical attachment.

2. The instrument of claim 1 wherein the first tissue forming surface and the second tissue forming surface are configured such that when tissue is placed between the first tissue forming surface and the complementary second tissue forming surface, the tissue is held in a form suitable as a valve repair material for at least one leaflet of a tri-leaflet valve.

3. The instrument of claim 1 wherein the first tissue forming surface and the second tissue forming surface are configured such that when tissue is placed between the first tissue forming surface and the complementary second tissue forming surface, the tissue is held in a form suitable as a valve repair material for at least one leaflet of a bi-leaflet valve.

4. The instrument of claim 1 wherein the piece of tissue is held in a configuration of at least one leaflet of a closed or partially closed circulatory system valve.

5. The instrument of claim 1 wherein the piece of tissue is precut in a preestablished geometrical pattern corresponding to the shape of at least one leaflet of a circulatory system valve.

6. The instrument of claim 1 further comprising a means for limiting the rotation of the first handle relative to the second handle.

7. The instrument of claim 1 wherein at least one tissue forming surface further comprises a tissue retention region.

8. The instrument of claim 7 wherein the tissue retention region comprises an area of ridges, pebbling, etches or grooves.

9. The instrument of claim 1 wherein the first handle is slidably engageable with the second handle.

10. The instrument of claim 9 wherein:

a) each tissue former has a back surface opposite the tissue forming surface, wherein the first handle is attached to the center of the tissue forming surface of the first former, and wherein the second handle is attached to the center of the back surface of the second former; and b) the handle of the second former has a hollow portion having a cross-sectional dimensions greater than the handle of the first former, such that the handle of the first former may be slidably engaged and inserted into the hollow portion of the handle of the second former.

11. The instrument of claim 10 wherein the handles have a corresponding polygonal shape.

* * * * *